US011117856B2

(12) United States Patent
Fleeman et al.

(10) Patent No.: US 11,117,856 B2
(45) Date of Patent: Sep. 14, 2021

(54) POLYAMINE COMPOUNDS TARGETING THE EFFLUX PUMPS OF MULTI-DRUG RESISTANT BACTERIAL PATHOGENS AND METHODS OF USING THE SAME

(71) Applicant: UNIVERSITY OF SOUTH FLORIDA, Tampa, FL (US)

(72) Inventors: Renee Fleeman, Tampa, FL (US); Radleigh G. Santos, Port St. Lucie, FL (US); Marcello Angelo Giulianotti, Port St. Lucie, FL (US); Lindsey Shaw, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/397,946

(22) Filed: Apr. 29, 2019

(65) Prior Publication Data
US 2019/0256452 A1   Aug. 22, 2019

Related U.S. Application Data

(63) Continuation of application No. PCT/US2017/065904, filed on Dec. 12, 2017.

(60) Provisional application No. 62/433,156, filed on Dec. 12, 2016.

(51) Int. Cl.
| | |
|---|---|
| *C07C 211/27* | (2006.01) |
| *A61P 31/04* | (2006.01) |
| *A61K 31/137* | (2006.01) |
| *A61K 45/06* | (2006.01) |
| *A61P 31/00* | (2006.01) |

(52) U.S. Cl.
CPC .......... *C07C 211/27* (2013.01); *A61K 31/137* (2013.01); *A61K 45/06* (2013.01); *A61P 31/00* (2018.01); *A61P 31/04* (2018.01); *Y02A 50/30* (2018.01)

(58) Field of Classification Search
None
See application file for complete search history.

(56) References Cited

U.S. PATENT DOCUMENTS 6,172,261 B1 * 1/2001 Vermeulin ............ C07C 233/36
506/15
2004/0204378 A1   10/2004 Nelson
2017/0298004 A1   10/2017 Tse-Dinh et al.

OTHER PUBLICATIONS

Ostresh et al. J. Org. Chem., 1998, 63, 24, 8622-8623.*
Nefzi et al, Tetrahedron 55 (1999), 335-344.*
Adabi et al., "Spread of Efflux Pump Overexpressing-Mediated Fluoroquinolone Resistance and Multidrug Resistance in Pseudomonas aeruginosa by using an Efflux Pump Inhibitor," Infection & Chemotherapy, 2015, 47(2): 98.
Adams et al., "Synthetic and Natural Product Approaches to the Development of Anti-Biofilm Agents," 9th Annual Graduate Student Research Symposium, University of South Florida, Mar. 20, 2017.
Amin, "P-glycoprotein Inhibition for Optimal Drug Delivery," Drug Target Insights, 2013, 7: 27-34.
Andersen et al., "Verapamil, a Ca2+ channel inhibitor acts as a local anesthetic and induces the sigma E dependent extra-cytoplasmic stress response in *E. coli*," Biochim Biophys Acta, 2006, 1758(10): 1587-1595.
Aparna et al., (2014). "Identification of Inhibitors for RND efflux pump of Pseudomonas aeruginosa using structure-based pharmacophore modeling approach," International Journal of Pharmacy and Pharmaceutical Sciences, 2014, 6(1): 84-89.
Askoura et al., "Efflux pump inhibitors (EPIs) as new antimicrobial agents againstPseudomonas aeruginosa," Libyan Journal of Medicine, 2011, 6(1): 8 pages.
Auerbach et al., "The structure of ribosome-lankacidin complex reveals ribosomal sites for synergistic antibiotics," Proceedings of the National Academy of Sciences, 2010, 107:1983-1988.
Blanchard et al., "Identification of Acinetobacter baumannii Serum-Associated Antibiotic Efflux Pump Inhibitors," Antimicrobial Agents and Chemotherapy, 2014, 58(11): 6360-6370.
Bogatcheva et al., "Identification of new diamine scaffolds with activity against Mycobacterium tuberculosis," J Med Chem, 2006, 49(11): 3045-3048.
Boucher et al., "Bad bugs, no drugs: no ESKAPE! An update from the Infectious Diseases Society of America," Clin Infect Dis, 2009, 48(1): 1-12.
C.T.F.A. Cosmetic Ingredient Handbook, 1992, pp. 587-592.
Chevalier et al., "Calcium-Channel Blockers and Cardiac Arrest Response," Circulation, 1999, 100(25): e140-e140.
ClinicalTrials.gov. "ClinicalTrials.gov. A service of the US National Institues of Health. NCT02092506," (2014).
Coban et al., "Effect of efflux pump inhibitor 1-(1-naphthylmethyl)-piperazine to MIC values of ciprofloxacin in ciprofloxacin resistant gram-negative bacteria," Mikrobiyol Bul, 2009, 43(3): 457-461.
Cornwell et al., "Certain calcium channel blockers bind specifically to multidrug-resistant human KB carcinoma membrane vesicles and inhibit drug binding to P-glycoprotein," J Biol Chem, 1987, 262(5): 2166-2170.
De Jonge et al., "Pyridodiazepine amines are selective therapeutic agents for helicobacter pylori by suppressing growth through inhibition of glutamate racemase but are predicted to require continuous elevated levels in plasma to achieve clinical efficacy," Antimicrob Agents Chemother, 2015, 59(4): 2337-2342.
Donnelly et al., "DNA vaccines," Ann. Rev. Immunol., 1997, 15: 617-648.
Falagas et al., "Pandrug-resistant Gram-negative bacteria: the dawn of the post-antibiotic era?" International Journal of Antimicrobial Agents, 2007, 29(6): 630-636.
Fernandes et al., "Antibiotics in late clinical development." Biochemical Pharmacology, 2017, 133: 152-163.

(Continued)

*Primary Examiner* — Clinton A Brooks
(74) *Attorney, Agent, or Firm* — Meunier Carlin & Curfman LLC

(57) ABSTRACT

Disclosed herein are efflux pump inhibitors and pharmaceutical compositions comprising the same. The efflux pump inhibitors may be used in methods of preventing antibiotic resistance in a subject, and in methods of treating a bacterial infection in a subject. The efflux pump inhibitor may be co-administered with an antibiotic.

19 Claims, 11 Drawing Sheets

(56) References Cited

OTHER PUBLICATIONS

Fleeman et al., "Combinatorial Libraries As a Tool for the Discovery of Novel, Broad-Spectrum Antibacterial Agents Targeting the ESKAPE Pathogens," J Med Chem, 2015, 58(8): 3340-3355.
Fleeman et al., "Identification of a Novel Polyamine Scaffold With Potent Efflux Pump Inhibition Activity Toward Multi-Drig Resistant Bacterial Pathogens," Frontiers in Microbiology, 2018, 9: 1301, 16 pages.
Fujita et al., "Remarkable synergies between baicalein and tetracycline, and baicalein and beta-lactams against methicillin-resistant *Staphylococcus aureus*," Microbiol Immunol, 2005, 49(4): 391-396.
Goldberg et al., "Sympathomimetic amines: potential clinical applications in ischemic heart disease," Am Heart J, 1982, 103(4 Pt 2): 724-729.
Gupta et al., "Acceleration of Tuberculosis Treatment by Adjunctive Therapy with Verapamil as an Efflux Inhibitor," American Journal of Respiratory and Critical Care Medicine, 2013, 188(5): 600-607.
Handzlik et al., "Recent Advances in Multi-Drug Resistance (MDR) Efflux Pump Inhibitors of Gram-Positive Bacteria *S. aureus*," Antibiotics, 2013, 2(1): 28-45.
Heagerty et al., "Time-dependent ROC curves for censored survival data and a diagnostic marker," Biometrics, 2000, 56(2): 337-44.
Hoel, "Statistical Aspects of Chemical Mixtures," Methods for assessing the effects of mixtures of chemicals, 1987, pp. 369-377.
Houghten et al., "Mixture-based synthetic combinatorial libraries," J Med Chem, 1999, 42(19): 3743-3778.
Houghten, "General method for the rapid solid-phase synthesis of large number of peptides: specificity of antigen-antibody interaction at the level of individual amino acids," Proc Natl Acad Sci U S A, 1985, 82:5131-5135.
International Search Report and Written Opinion for Application No. PCT/US2017/065904 dated Mar. 23, 2018 (23 pages).
IUPAC 1974 Recommendations for Section E, Fundamental Stereochemistry, in Pure Appl. Chem., 1976, 45, 13-30.
Jackson et al., "Biofilm formation and dispersal under the influence of the global regulator CsrA of *Escherichia coli*," J Bacteriol, 2002, 184:290-301.
Kishen et al., "Efflux Pump Inhibitor Potentiates Antimicrobial Photodynamic Inactivation of Enterococcus faecalis Biofilm," Photochemistry and Photobiology, 2010, 86: 1343-1349.
Kjelleberg et al., "Is there a role for quorum sensing signals in bacterial biofilms?" Curr Opin Microbiol, 2002, 5: 254-258.
Kourtesi, "Microbial Efflux Systems and Inhibitors: Approaches to Drug Discovery and the Challenge of Clinical Implementation," The Open Microbiology Journal, 2013, 7(1): 34-52.
Kumar et al., "A Review on Efflux Pump Inhibitors of Gram-Positive and Gram-Negative Bacteria from Plant Sources," International Journal of Current Microbiology and Applied Sciences, 2016, 5(6): 837-855.
Kumar et al., "Biochemistry of Bacterial Multidrug Efflux Pumps," International Journal of Molecular Sciences, 2012, 13(12): 4484-4495.
Kwon et al., "Polyamine Effects on Antibiotic Susceptibility in Bacteria." Antimicrobial Agents and Chemotherapy, 2007, 51(6): 2070-2077.
Kyte et al., "A simple method for displaying the hydropathic character of a protein," J. Mol. Biol., 1982, 157, 105-132.
Lamers et al., "The Efflux Inhibitor Phenylalanine-Arginine Beta-Naphthylamide (PAβN) Permeabilizes the Outer Membrane of Gram-Negative Bacteria," PLoS ONE, 2013, 8(3): e60666.
Lebeaux et al., "From in vitro to in vivo Models of Bacterial Biofilm-Related Infections," Pathogens, 2013, 2(2): 288-356.
Li et al., "Comparison of carbon-sulfur and carbon-amine bond in therapeutic drug: 4β-S-aromatic heterocyclic podophyllum derivatives display antitumor activity," Scientific Reports, 2015, 5: 14814.
Lister et al., "Antibacterial-Resistant Pseudomonas aeruginosa: Clinical Impact and Complex Regulation of Chromosomally Encoded Resistance Mechanisms," Clinical Microbiology Reviews, 2009, 22(4): 582-610.
Liu et al., "Synergistic Activities of an Efflux Pump Inhibitor and Iron Chelators against Pseudomonas aeruginosa Growth and Biofilm Formation," Antimicrobial Agents and Chemotherapy, 2010, 54: 3960-3963.
Lomovskaya et al., "Identification and Characterization of Inhibitors of Multidrug Resistance Efflux Pumps in Pseudomonas aeruginosa: Novel Agents for Combination Therapy," Antimicrobial Agents and Chemotherapy, 2001, 45(1): 105-116.
Machado et al., "Mode of action of the 2-phenylquinoline efflux inhibitor PQQ4R against *Escherichia coli*." PeerJ, 2017, 5: e3168.
Manku et al., "A mild and general solid-phase method for the synthesis of chiral polyamines. Solution studies on the cleavage of borane-amine intermediates from the reduction of secondary amides," J Org Chem, 2001, 66:874-885.
Masuda et al., "Substrate specificities of MexAB-OprM, MexCD-OprJ, and MexXY-oprM efflux pumps in Pseudomonas aeruginosa," Antimicrob Agents Chemother, 2000, 44(12): 3322-3327.
McCutcheon's vol. 1, Emulsifiers & Detergents, 1994, North American Edition, pp. 236-239.
McMurry et al., "Active efflux of tetracycline encoded by four genetically different tetracycline resistance determinants in *Escherichia coli*," Proc Natl Acad Sci U S A, 1980, 77(7): 3974-3977.
Minagawa et al., "RND type efflux pump system MexAB-OprM of pseudomonas aeruginosa selects bacterial languages, 3-oxo-acyl-homoserine lactones, for cell-to-cell communication," BMC Microbiology, 2012, 12:70.
Misra et al., "Assembly and transport mechanism of tripartite drug efflux systems." Biochimica et Biophysica Acta (BBA)—Proteins and Proteomics, 2009, 1794(5): 817-825.
Moore et al., "Active Efflux Influences the Potency of Quorum Sensing Inhibitors in Pseudomonas aeruginosa," ChemBioChem, 2014, 15:435-442.
Nakashima et al., "Structural basis for the inhibition of bacterial multidrug exporters," Nature, 2013, 500(7460): 102-106.
Nakayama et al., "MexAB-OprM specific efflux pump inhibitors in Pseudomonas aeruginosa. Part 2: achieving activity in vivo through the use of alternative scaffolds," Bioorganic & Medicinal Chemistry Letters, 2003, 13: 4205-4208.
Nefzi et al., "Parallel solid phase synthesis of tetrasubstituted diethylenetriamines via selective amide alkylation and exhaustive reduction of N-acylated dipeptides," Tetrahedron, 1999, 55: 335-344.
Nefzi et al., "Solid-phase synthesis of bis-heterocyclic compounds from resin-bound orthogonally protected lysine," J Comb Chem, 2001, 3: 68-70.
Nefzi et al., "The Current Status of Heterocyclic Combinatorial Libraries," Chem Rev, 1997, 97: 449-472.
Nelson et al., "Inhibition of the tetracycline efflux antiport protein by 13-thio-substituted 5-hydroxy-6-deoxytetracyclines," J Med Chem, 1993, 36(3): 370-377.
Nelson et al., "Molecular requirements for the inhibition of the tetracycline antiport protein and the effect of potent inhibitors on the growth of tetracycline-resistant bacteria," J Med Chem, 1994, 37(9): 1355-1361.
Nelson et al., "Reversal of tetracycline resistance mediated by different bacterial tetracycline resistance determinants by an inhibitor of the Tet(B) antiport protein," Antimicrob Agents Chemother, 1999, 43(7): 1719-1724.
Neyrolles et al., "Ion Channel Blockers as Antimicrobial Agents, Efflux Inhibitors, and Enhancers of Macrophage Killing Activity against Drug Resistant Mycobacterium tuberculosis," Plos One, 2016, 11(2): e0149326.
Nikaido et al., "Broad-specificity efflux pumps and their role in multidrug resistance of Gram-negative bacteria," FEMS Microbiol Rev, 2012, 36(2): 340-363.
Olofsson et al., "Optimizing Drug Exposure to Minimize Selection of Antibiotic Resistance," Clinical Infectious Diseases, 2007, 45(Supplement 2): S129-S136.
Opperman et al., "Characterization of a Novel Pyranopyridine Inhibitor of the AcrAB Efflux Pump of *Escherichia coli*," Antimicrobial Agents and Chemotherapy, 2013, 58(2): 722-733.
Opperman et al., "Recent advances toward a molecular mechanism of efflux pump inhibition," Frontiers in Microbiology, 2015, 6: 421.

(56) References Cited

OTHER PUBLICATIONS

Ostresh et al., "Solid-Phase Synthesis of Trisubstituted Bicyclic Guanidines via Cyclization of Reduced N-Acylated Dipeptides," The Journal of Organic Ohemistry, 1998, 63: 8622-8623.

Palmer et al., "Metabolism and Pathogenicity of Pseudomonas aeruginosa Infections in the Lungs of Individuals with Cystic Fibrosis," Microbiol Spectr, 2015, 3(4): 185-213.

Pankey et al., "Clinical Relevance of Bacteriostatic versus Bactericidal Mechanisms of Action in the Treatment of Gram-Positive Bacterial Infections," Clinical Infectious Diseases, 2004, 38(6): 864-870.

Pegg, "Toxicity of Polyamines and Their Metabolic Products," Chemical Research in Toxicology, 2013, 26(12): 1782-1800.

Poulikakos et al., "Aminoglycoside therapy in infectious diseases," Expert Opinion on Pharmacotherapy, 2013, 14(12): 1585-1597.

Reardon, "WHO warns against 'post-antibiotic' era," Nature, 2014, 3 pages.

Reilley et al., "Identification of two novel, potent, low-liability antinociceptive compounds from the direct in vivo screening of a large mixture-based combinatorial library," AAPS J, 2010, 12(3): 318-329.

Remington's Pharmaceutical Sciences, 15th Ed. 1975, pp. 335-337.

Renau et al., "Inhibitors of Efflux Pumps in Pseudomonasaeruginosa Potentiate the Activity of the Fluoroquinolone Antibacterial Levofloxacin," Journal of Medicinal Chemistry, 1999, 42(24): 4928-4931.

Rockey et al., "Polyamines Inhibit Porin-Mediated Fluoroquinolone Uptake in Mycobacteria," PLoS ONE, 2013, 8(6): e65806.

Rossolini et al., "Update on the antibiotic resistance crisis," Current Opinion in Pharmacology, 2014, 18: 56-60.

Sandhaus et al., "Small-Molecule Inhibitors Targeting Topoisomerase I as Novel Antituberculosis Agents," Antimicrobial Agents and Chemotherapy, 2016, 60: 4028-4036.

Santos et al., "The mathematics of a successful deconvolution: a quantitative assessment of mixture-based combinatorial libraries screened against two formylpeptide receptors," Molecules, 2013, 18(6): 6408-6424.

Sjuts et al., "Molecular basis for inhibition of AcrB multidrug efflux pump by novel and powerful pyranopyridine derivatives," Proceedings of the National Academy of Sciences, 2016, 113(13): 3509-3514.

Soto, "Role of efflux pumps in the antibiotic resistance of bacteria embedded in a biofilm," Virulence, 2013, 4(3): 223-229.

Spellberg et al., "The Epidemic of Antibiotic-Resistant Infections: A Call to Action for the Medical Community from the Infectious Diseases Society of America," Clinical Infectious Diseases, 2008, 46(2): 155-164.

Sugimura et al., "Macrolide Antibiotic-Mediated Downregulation of MexAB-OprM Efflux Pump Expression in Pseudomonas aeruginosa," Antimicrobial Agents and Chemotherapy, 2008, 52: 4141-4144.

Sun et al., "Bacterial multidrug efflux pumps: Mechanisms, physiology and pharmacological exploitations," Biochemical and Biophysical Research Communications, 2014, 453(2): 254-267.

Thomas et al., "Polyamines in cell growth and cell death: molecular mechanisms and therapeutic applications," Cellular and Molecular Life Sciences, 2001, 58(2): 244-258.

Tommasi et al., "ESKAPEing the labyrinth of antibacterial discovery." Nat Rev Drug Discov, 2015, 14(8): 529-542.

Truong-Bolduc et al., "Native Efflux Pumps Contribute Resistance to Antimicrobials of Skin and the Ability of Staphylococcus aureus to Colonize Skin," Journal of Infectious Diseases, 2013, 209(9): 1485-1493.

Ughachukwu et al., "Efflux pump-mediated resistance in chemotherapy," Annals of Medical and Health Sciences Research, 2012, 2(2): 191.

Van Bambeke et al., "Inhibitors of bacterial efflux pumps as adjuvants in antibiotic treatments and diagnostic tools for detection of resistance by efflux," Recent Pat Antiinfect Drug Discov, 2006, 1(2): 157-175.

Van Horn et al., "Antibacterial Activity of a Series of N2,N4-Disubstituted Quinazoline-2,4-diamines," Journal of Medicinal Chemistry, 2014, 57(7): 3075-3093.

Vazquez-Laslop, "Efflux of the Natural Polyamine Spermidine Facilitated by the Bacillus subtilis Multidrug Transporter Blt," Journal of Biological Chemistry, 1997, 272(14): 8864-8866.

Venter et al., "RND-type drug efflux pumps from Gram-negative bacteria: molecular mechanism and inhibition," Frontiers in Microbiology, 2015, 6: 377.

Ventola, "The antibiotic resistance crisis: part 1: causes and threats." P T, 2015, 40(4): 277-283.

Vettoretti et al., "Efflux Unbalance in Pseudomonas aeruginosa Isolates from Cystic Fibrosis Patients," Antimicrobial Agents and Chemotherapy, 2009, 53: 1987-1997.

Von Salm et al., "Darwinolide, a New Diterpene Scaffold That Inhibits Methicillin-Resistant Staphylococcus aureus Biofilm from the Antarctic Sponge Dendrilla membranosa," Org Lett, 2016, 18(11): 2596-2599.

Watkins et al., "The relationship between physicochemical properties, In vitro activity and pharmacokinetic profiles of analogues of diamine-Containing efflux pump inhibitors," Bioorganic & Medicinal Chemistry Letters, 2003, 13(23): 4241-4244.

Webber et al., "The Efflux Inhibitor Phenylalanine-Arginine Beta-Naphthylamide (PAβN) Permeabilizes the Outer Membrane of Gram-Negative Bacteria," PLoS ONE, 2013, 8(3): e60666.

Weinstein et al., "Efflux Pumps and Nosocomial Antibiotic Resistance: A Primer for Hospital Epidemiologists," Clinical Infectious Diseases, 2005, 40(12): 1811-1817.

Worthington et al., "Combination approaches to combat multidrug-resistant bacteria," Trends in Biotechnology, 2013, 31(3): 177-184.

Wu et al., "Scaffold ranking and positional scanning utilized in the discovery of nAChR-selective compounds suitable for optimization studies," J Med Chem, 2013, 56(24): 10103-10117.

Yoneyama et al., "Antibiotic Resistance in Bacteria and Its Future for Novel Antibiotic Development," Bioscience, Biotechnology and Biochemistry, 2014, 70(5): 1060-1075.

* cited by examiner

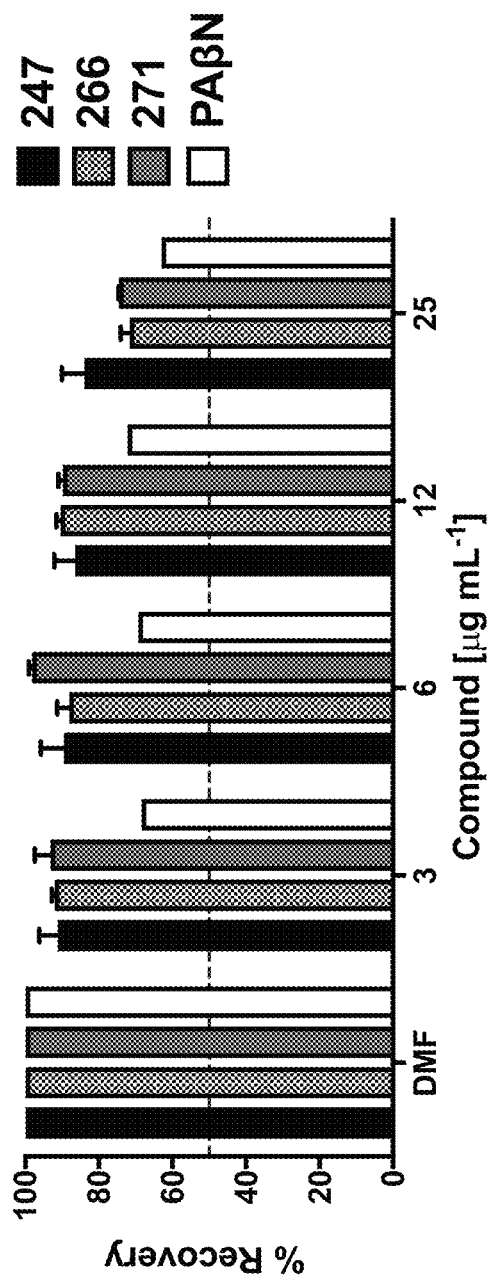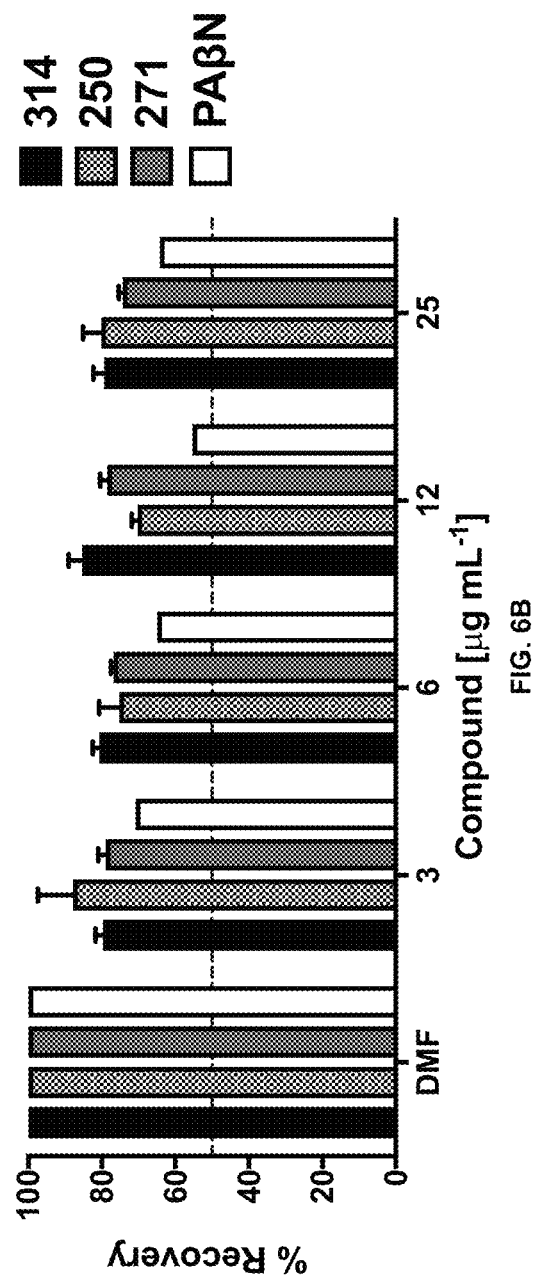
FIG. 6A
FIG. 6B

POLYAMINE COMPOUNDS TARGETING THE EFFLUX PUMPS OF MULTI-DRUG RESISTANT BACTERIAL PATHOGENS AND METHODS OF USING THE SAME

CROSS-REFERENCE TO RELATED APPLICATIONS

This application is a continuation of International Application No. PCT/US2017/065904, filed Dec. 12, 2017, which claims priority to U.S. Provisional Patent Application No. 62/433,156, filed Dec. 12, 2016, the content of which are incorporated herein by reference in their entirety.

STATEMENT REGARDING FEDERALLY SPONSORED RESEARCH

This invention was made with government support under grant AI103715 awarded by the National Institutes of Health, and grant AI080626 awarded by the National Institutes of Health. The government has certain rights in the invention.

FIELD

This disclosure relates to efflux pump inhibitor compounds and methods of using the same for preventing antibiotic resistance.

INTRODUCTION

The continued increase of antimicrobial resistant bacterial infections is an ongoing public health crisis in the U.S. with mortality rates. This problem can be directly linked to the ever growing demands for antibiotics, coupled with a diminishing therapeutic arsenal that has been exacerbated by a continual decline in antibiotic discovery over the past 30 years. This presents the scenario of a post-antibiotic era, where conventional antibiotics may no longer be effective, and common infections may once again become fatal. One issue is that typical drug discovery efforts often result in the development of therapeutics with known mechanisms of action, thus allowing bacteria to rapidly evolve resistance to these new agents. Consequently, new strategies are urgently needed for the discovery of novel therapeutics targeting multi-drug resistant organisms.

The selective pressure antibiotics place on heterogeneous bacterial communities often directly leads to resistant clones becoming dominant within infectious populations. Novel therapeutics targeting resistant bacterial strains would be therapeutically advantageous, specifically focusing on those isolates that prove the most difficult to eradicate. A unique way to do this is to interfere with bacterial resistance mechanisms, rather than focusing on bacterial viability. Such treatment options could restore the effectiveness of numerous obsolete clinical antibiotics, reclaiming many important therapeutics. Co-administration of such anti-resistance agents alongside existing antibiotics may also lead to decreased resistance, as multiple targets within the cell are impacted simultaneously. Hence, anti-resistance approaches may exponentially increase the number of available therapeutic options, whereas conventional antibiotic development commonly yields only a single new drug.

A method by which bacteria can resist the action of antibacterial agents is via efflux pump extrusion. Efflux pumps (EPs) are complexes within the bacterial cell envelope used to export toxic substances such as antibiotics from the intracellular environment before damage to the cell occurs. EPs are found in most multi-drug resistant nosocomial pathogens, with many EPs having similar and overlapping substrate specificities. As such, targeting bacterial EPs via therapeutic intervention could effectively re-sensitize cells to a broad spectrum of antibacterial agents. Recent studies have shown that strains overexpressing EPs commonly display an average >2-fold increased minimal inhibitory concentrations (MIC) towards multiple antibiotics.

Efflux mediated resistance was first indicated in a study demonstrating that tetracycline insensitivity could result from plasmid-encoded transport systems. Following this, it was observed that polyamine tetracycline derivatives could increase the effectiveness of tetracycline when administered concomitantly. Early inhibitors targeting EPs, such as reserpine, were discovered from existing conventional drugs; however their use was limited by the need for administration at very high doses in order to be effective. They also suffered from off-target effects, with compounds such as verapamil, reserpine, and thioridazine not only inhibiting bacterial EPs, but eukaryotic transporters as well. For example, EPs such as verapamil when administered at higher doses have been shown to cause cardiac arrest due to calcium channel inhibition. More recent agents, such as MC-207, 110 (phenylalanine arginine beta naphthalamide, or PaβN), have been shown to have increased specificity towards bacterial efflux systems; however, the advancement of this scaffold has been abandoned as it has been shown to non-specifically depolarize prokaryotic membranes and cause significant nephrotoxicity. Although a number of EP inhibitors with improved activity have been identified in recent years, the only advancement into clinical trials to date has been for the proton pump inhibitor omeprazole, used in combination with amoxicillin and clarithromycin to treat *Helicobacter pylori* infections.

There is a need to identify new efflux pump inhibitors (EPIs) with enhanced properties and limited toxicity. This is particularly true for Gram negative species, such as *Pseudomonas aeruginosa*, which have impermeable outer membranes and commonly overexpress efflux systems. Indeed, *P. aeruginosa* has 10 Resistance nodulation division (RND) EPs that collectively extrude β-lactams, fluoroquinolones, SDS, tetracycline, erythromycin, ethidium bromide, crystal violet, and homoserine lactones. Moreover, given the broad substrate range of *P. aeruginosa* EPs, the inhibition of one pump may be alleviated by the upregulation of additional EPs with parallel targets.

SUMMARY

In an aspect, the disclosure relates to a compound according to Formula I:

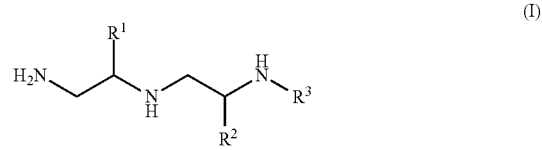

(I)

or a pharmaceutically acceptable salt thereof, wherein $R^1$ is $-(CH_2)_n-Y$; Y is methyl, $-NH-X$, cycloalkyl, aryl, or heteroaryl; X is H or methyl; n is an integer from 0 to 10; $R^2$ is $-(CH_2)_m-Z$; Z is cycloalkyl, aryl, heteroaryl, or amino; m is an integer from 0 to 5; $R^3$ is —$(CH_2)_p$-Q; Q is cycloalkyl, aryl, heteroaryl, or amino; and p is an integer from 0 to 5.

In some embodiments, the compound is according to Formula Ia:

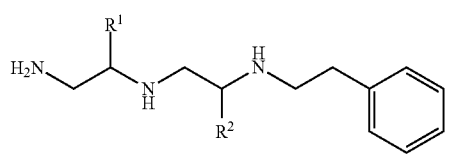

(Ia)

or a pharmaceutically acceptable salt thereof, wherein $R^1$ is —$(CH_2)_n$—Y; Y is methyl, —NH—X, cycloalkyl, aryl, or heteroaryl; X is H or methyl; n is an integer from 0 to 10; $R^2$ is —$(CH_2)_m$—Z; Z is cycloalkyl, aryl, heteroaryl, or amino; and m is an integer from 0 to 5.

In some embodiments, Y is —NH—X, wherein X is methyl. In some embodiments, Y is —NH—X, wherein X is H. In some embodiments, Y is aryl. In some embodiments, Y is phenyl. In some embodiments, Z is aryl. In some embodiments, Z is phenyl. In some embodiments, Z is amino. In some embodiments, Q is aryl. In some embodiments, Q is phenyl.

In some embodiments, the carbon atom to which R1 is attached has (S) configuration. In some embodiments, the carbon atom to which R1 is attached has (R) configuration. In some embodiments, the carbon atom to which R2 is attached has (S) configuration. In some embodiments, the carbon atom to which R1 is attached has (S) configuration, and the carbon atom to which R2 is attached has (S) configuration. In some embodiments, the carbon atom to which R1 is attached has (R) configuration, and the carbon atom to which R2 is attached has (S) configuration.

In some embodiments, R1 is —(CH2)n-Y, Y is —NH—X, X is methyl, n is 4, R2 is —(CH2)m-Z wherein Z is phenyl and m is 1, and R3 is —(CH2)p-Q wherein Q is phenyl and p is 2. In some embodiments, R1 is —(CH2)n-Y, Y is —NH—X, X is H, n is 2, R2 is —(CH2)m-Z wherein Z is phenyl and m is 1, and R3 is —(CH2)p-Q wherein Q is phenyl and p is 2. In some embodiments, R1 is —(CH2)n-Y, Y is —NH—X, X is methyl, n is 4, R2 is —(CH2)m-Z wherein Z is phenyl and m is 1, and R3 is —(CH2)p-Q wherein Q is phenyl and p is 2. In some embodiments, R1 is —(CH2)n-Y, Y is —NH—X, X is H, n is 3, R2 is —(CH2)m-Z wherein Z is phenyl and m is 1, and R3 is —(CH2)p-Q wherein Q is phenyl and p is 2. In some embodiments, R1 is —(CH2)n-Y, Y is phenyl, n is 1, R2 is —(CH2)m-Z wherein Z is amino and m is 3, and R3 is —(CH2)p-Q wherein Q is phenyl and p is 2. In some embodiments, R1 is —(CH2)n-Y, Y is —NH—X, X is methyl, n is 4, and R2 is —(CH2)m-Z wherein Z is phenyl and m is 1. In some embodiments, R1 is —(CH2)n-Y, Y is —NH—X, X is H, n is 2, and R2 is —(CH2)m-Z wherein Z is phenyl and m is 1. In some embodiments, R1 is —(CH2)n-Y, Y is —NH—X, X is methyl, n is 4, and R2 is —(CH2)m-Z wherein Z is phenyl and m is 1. In some embodiments, R1 is —(CH2)n-Y, Y is —NH—X, X is H, n is 3, and R2 is —(CH2)m-Z wherein Z is phenyl and m is 1. In some embodiments, R1 is —(CH2)n-Y, Y is phenyl, n is 1, and R2 is —(CH2)m-Z wherein Z is amino and m is 3.

In some embodiments, the compound or a pharmaceutically acceptable salt thereof is selected from the following:

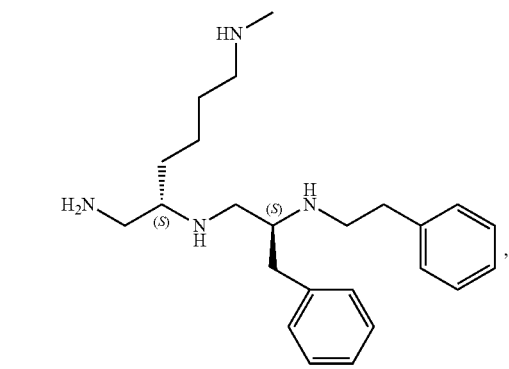

247

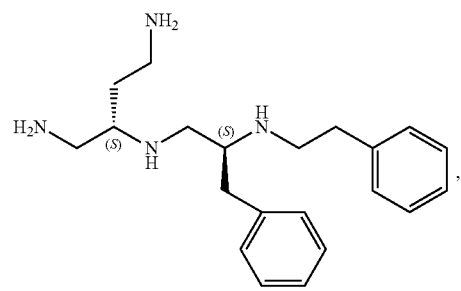

250

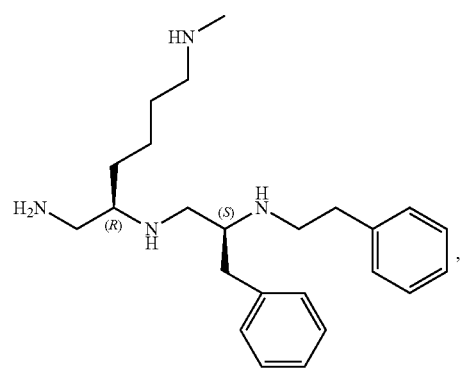

266

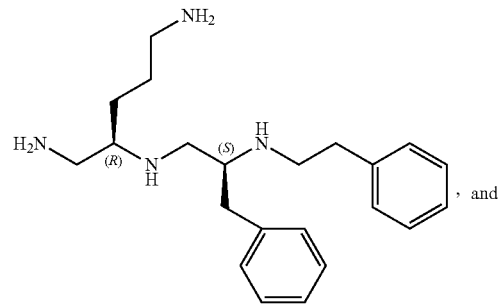

271
, and

-continued

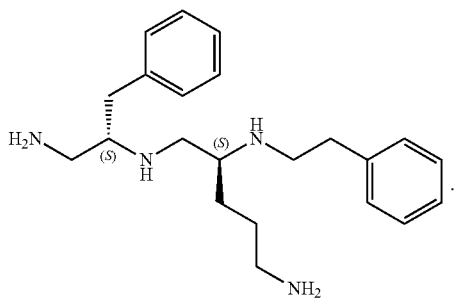

314

In some embodiments, the compound or the salt is an anti-resistance molecule. In some embodiments, the compound or the salt is an efflux pump inhibitor. In some embodiments, the compound or the salt is a bacterial efflux pump inhibitor. In some embodiments, the compound or the salt does not disrupt bacterial membrane polarity. In some embodiments, the compound or the salt is not toxic to a mammalian cell. In some embodiments, the compound or the salt does not inhibit a mammalian efflux pump. In some embodiments, the compound or the salt does not inhibit a mammalian calcium ion channel. In some embodiments, the compound or the salt has no antibacterial activity itself. In some embodiments, the compound or the salt reduces the therapeutic amount of an antibiotic by at least 3-fold. In some embodiments, the therapeutic amount is reduced by at least 5-fold. In some embodiments, the therapeutic amount is reduced by at least 8-fold. In some embodiments, the compound or the salt reduces the minimum inhibitory concentration (MIC) of an antibiotic by at least 3-fold. In some embodiments, the MIC is reduced by at least 5-fold. In some embodiments, the MIC is reduced by at least 8-fold.

In a further aspect, the disclosure relates to a pharmaceutical composition comprising a therapeutically effective amount of a compound as detailed herein, or a pharmaceutically acceptable salt thereof, and a pharmaceutically acceptable carrier. In some embodiments, the pharmaceutical composition further includes an antibiotic.

Another aspect of the disclosure provides a method of preventing antibiotic resistance in a subject. The method may include administering to the subject a therapeutically effective amount of a compound as detailed herein, or a pharmaceutically acceptable salt thereof, or a pharmaceutical composition as detailed herein.

Another aspect of the disclosure provides a method of treating a bacterial infection in a subject. The method may include administering to the subject a therapeutically effective amount of a compound as detailed herein, or a pharmaceutically acceptable salt thereof, or a pharmaceutical composition as detailed herein.

In some embodiments, the compound, or the salt, or the composition is co-administered with at least one antibiotic.

The disclosure provides for other aspects and embodiments that will be apparent in light of the following detailed description and accompanying figures.

BRIEF DESCRIPTION OF THE DRAWINGS

FIG. 6A and FIG. 6B are graphs showing that the lead polyamines lack general toxicity towards eukaryotic cells. Shown is the percent recovery of Hek293T cells (FIG. 6A) and HepG2 cells (FIG. 6B) when tested using a MTT cytotoxicity assay following treatment with polyamine leads. Conversion of MTT to formazan was assessed and converted to percent recovery using 0.01% Triton 100X as 100% death, and no treatment (DMF) as 100% survival. These controls were used to calculate percent recovery, and to determine $LD_{50}$s (dotted line). Data is from at least three biological replicates, with error bars shown ±SEM.

DETAILED DESCRIPTION

Figure 1:
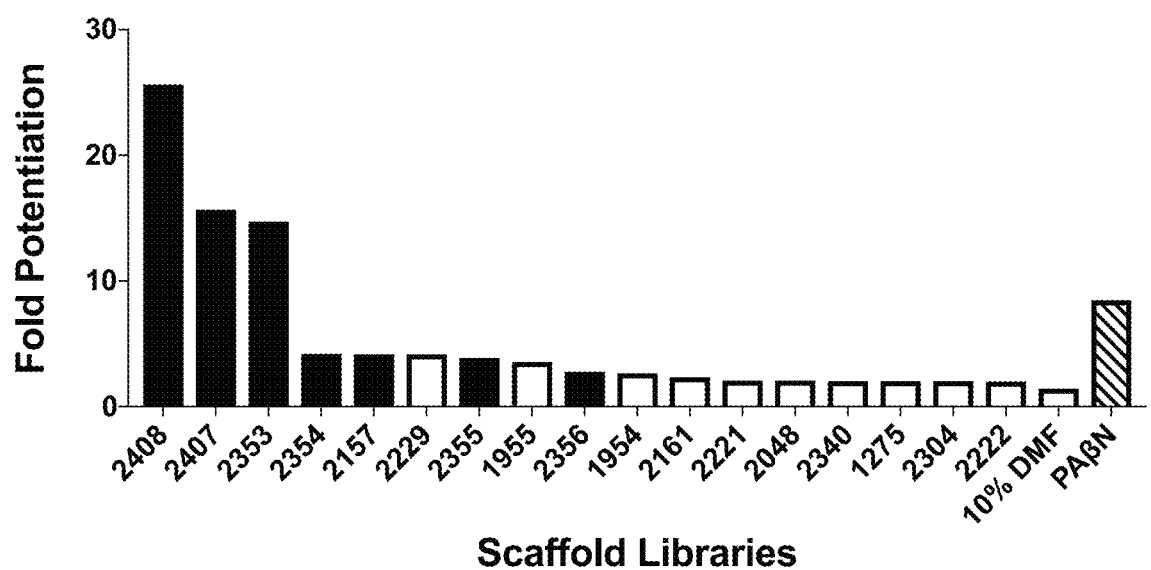
FIG. 1 is a graph showing the screening of combinatorial libraries to identify scaffolds that inhibit bacterial efflux pumps. The Torrey Pines scaffold libraries (TPL) were screened for potentiation of tetracycline activity against a clinical tetracycline-resistant *P. aeruginosa* isolate. Data is represented as fold potentiation, which is defined as the $EC_{90}$ tetracycline concentration+TPL/the $EC_{90}$ tetracycline concentration (no TPL). In each assay, the TPL concentration used was 25 µg mL$^{-1}$. The libraries represented by a black bar displayed inhibition of bacterial growth themselves, in the absence of tetracycline, whilst white bars represent libraries that display no inhibition of bacterial growth. Positive (PAβN) and negative (10% DMF) control compounds were used, and are denoted by black lined bars. Note that only libraries displaying 2-fold or greater potentiation are shown.

Provided herein are new anti-resistance molecules, and in particular, efflux pump inhibitors. Using high throughput screening against multi-drug resistant *P. aeruginosa*, we identified a polyamine scaffold that demonstrated strong efflux pump inhibition without possessing any antibacterial effects or toxic effects. From a library of 188 compounds, we studied the properties of 5 lead compounds in detail, observing a 5- to 8-fold decrease in the 90% effective concentration of both tetracycline and chloramphenicol towards *P. aeruginosa* isolates. Using ethidium bromide accumulation assays we determined that the compounds were not only active against *P. aeruginosa* efflux pumps, but against those from *A. baumannii* and *S. aureus* as well. The efflux pump inhibitors as detailed herein display no disruption of bacterial membrane polarity, no general toxicity towards mammalian cells, and no inhibition of calcium channel activity in human embryonic kidney cells. Combination treatment with the efflux pump inhibitors as detailed herein engendered a marked increase in the bactericidal capacity of tetracycline, and significantly decreased viability within *P. aeruginosa* biofilms. As such, detailed herein are novel compounds with broad and specific efflux pump inhibiting activity, whilst at the same time having limited cytotoxicity towards eukaryotic cells, thereby lacking problematic off-target effects that have been an issue with conventional molecules. The efflux pump inhibitors may be used to prevent antibiotic resistance, and they may be used in combination with an antibiotic to treat a pathological condition in a subject.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 7$^{th}$ Edition, John Wiley & Sons, Inc., New York, 2013; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" or "alkoxyl" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_1$-$C_6$ alkyl" means a straight or branched chain hydrocarbon containing from 1 to 6 carbon atoms. The term "$C_1$-$C_4$ alkyl" means a straight or branched chain hydrocarbon containing from 1 to 4 carbon atoms. The term "$C_1$-$C_3$ alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "alkylamino," as used herein, means at least one alkyl group, as defined herein, is appended to the parent molecular moiety through an amino group, as defined herein.

The term "alkylene" as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino" as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl" as used herein, refers to an aromatic group such as a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl, and tetrahydroquinolinyl.

The term "carboxyl" as used herein, means a carboxylic acid, or —COOH.

The term "cycloalkyl" means a monovalent saturated hydrocarbon ring or a bicyclic group. Cycloalkyl groups have zero heteroatoms and zero double bonds. Cycloalkyl groups are monocyclic, or are fused, spiro, or bridged bicyclic ring systems. Monocyclic cycloalkyl groups contain 3 to 10 carbon atoms, preferably 4 to 7 carbon atoms, and more preferably 5 to 6 carbon atoms in the ring. Bicyclic cycloalkyl groups contain 8 to 12 carbon atoms, preferably 9 to 10 carbon atoms in the ring. Cycloalkyl groups may be substituted or unsubstituted. Cycloalkyl groups include, for example, cyclopropyl, cyclobutyl, cyclopentyl, cyclohexyl, and cycloheptyl.

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, and cycloheptenyl.

The term "cycloalkynyl," as used herein, means a monocyclic or multicyclic ring system containing at least one carbon-carbon triple bond and preferably having from 5-10 carbon atoms per ring or more than 10 carbon atoms per ring.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" or "halo" as used herein, means Cl, Br, I, or F.

The term "heteroalkyl" as used herein, means an alkyl group, as defined herein, in which at least one of the carbons of the alkyl group is replaced with a heteroatom, such as oxygen, nitrogen, and sulfur. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system containing at least one heteroatom independently selected from the group consisting of N, O, and S. The aromatic monocyclic rings are five or six membered rings containing at least one heteroatom independently selected from the group consisting of N, O, and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic" or "heterocyclyl" as used herein means a monocyclic heterocycle, a bicyclic heterocycle (heterobicyclic), or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^3$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroarylalkyl" as used herein, refers to a heteroaryl group, as defined herein, appended to the parent molecular moiety through an alkylene group, as defined herein.

The term "heterocyclylalkyl" as used herein, refers to a heterocycle group, as defined herein, appended to the parent molecular moiety through an alkylene group, as defined herein.

The term "hydroxyl" or "hydroxy" as used herein, means an —OH group.

The term "hydroxyalkyl" as used herein, means at least one —OH group, is appended to the parent molecular moiety through an alkylene group, as defined herein.

The term "nitro" means a —NO$_2$ group.

In some instances, the number of carbon atoms in a hydrocarbyl substituent (e.g., alkyl or cycloalkyl) is indicated by the prefix "C$_x$-C$_y$—", wherein x is the minimum and y is the maximum number of carbon atoms in the substituent. Thus, for example, "C$_1$-C$_3$ alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

"Adjuvant" as used herein refers to a substance that enhances a subject's response toward a specific active agent. In some embodiments, an adjuvant is a substance that enhances a subject's response toward an antibiotic. In some embodiments, an adjuvant is a substance that enhances, augments, or potentiates the subject's immune response to a vaccine antigen.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "antagonist" or "inhibitor" refers to a molecule which blocks (e.g., reduces or prevents) a biological activity.

As used herein, the term "agonist" refers to a molecule or compound that triggers (e.g., initiates or promotes), partially or fully enhances, stimulates, or activates one or more biological activities. An agonist may mimic the action of a naturally occurring substance. Whereas an agonist causes an action, an antagonist blocks the action of the agonist.

"Antimicrobial" or "antibiotic" refers to a substance or method that is able to kill or inhibit the growth of microorganisms. To "kill or inhibit the growth of" includes limiting the presence of at least one microorganism. To "kill or inhibit the growth of" also includes inactivation and prevention of the replication of or reducing the number of a microorganism. Antibiotics include, for example, penicillin such as penicillin G, penicillin V, penicillin G benzathine, ampicillin, anoxacillin, nafcillin, carbenicilllin, dicloxacillin, bacampicillin, piperacillin, ticaricillin, mezlocillin and the like; cephalosporins such as cefazolin, cefadroxil, cephalexin, cefaclor, cefoxitin, cefonicid, ceftizoxime, cefprozil, ceftazidine, cefixime, cefpodoxime proxitel and the like; aminoglycosides such as amikacin, gentamicin, tobramycin, netilmicin, streptomycin and the like; macrolides such as erythromycin and the like; monobactams such as aztreonam and the like; rifamycin and derivatives such as rifampin, rifamide, rifaximin and the like; chloramphenicol, clindamycin, lincomycin, imipenem, vancomycin; tetracyclines such as chloretetracycline, tetracycline, minocycline, doxycycline and the like; fusidic acid, novobiocin and the like; fosfomycin, fusidate sodium, neomycin, bacitracin, polymyxin, capreomycin, colistimethate, colistin, sulfamethoxazole, trimethoprim, and gramicidin, and combinations thereof.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be an subject or cell without an inhibitor as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

"Microorganism" refers to a unicellular or multi-cellular microscopic or macroscopic life form. Microorganisms include, for example, bacteria, protobacteria, phytoplankton, fungi, viruses, algae, molds, oomycetes, parasites, nematodes, and protozoans, or any combination thereof. Microorganisms may also be referred to as microbes.

Bacteria include Gram-negative bacteria, Gram-positive bacteria, aerobic bacteria, anaerobic bacteria, sulfate-reducing bacteria, nitrate-reducing bacteria, or any combination thereof. Bacteria may include pathogenic bacteria, which can cause an infection or a pathological condition in a subject. "Gram-positive" is a taxonomic feature referring to bacteria which resist decolorization with any standard Gram-staining dyes. In contrast, Gram-negative bacteria are easily decolorized with certain organic solvents such as, for example, ethanol or acetone. The ability of bacteria to retain or resist staining generally reflects the structure of the cell wall, and it has been suggested that Gram-negative bacteria have more extensive peptidoglycan crosslinking and less permeable cell walls than their Gram-negative counterparts. In some embodiments, the efflux pump is a Gram-negative bacterial efflux pump. In some embodiments, the efflux pump is a Gram-positive bacterial efflux pump.

Gram-negative bacteria include, for example, *Acinetobacter* spp. (*A. baumannii*); *Bacterioides* spp. (*B. fragilis*); *Bordetella* spp. (*B. pertussis*); *Borrelia* spp. (*B. burgdorferi, B. garinii, B. afzelii*); *Brucella* spp. (*B. abortus, B. canis, B. melitensis, B. suis*); *Burkholderia* spp. (*B. mallei, B. pseudomallei*); *Calymmatobacterium* spp.; *Campylobacter* spp. (*C. fetus, C. jejuni*); *Chlamydia* spp. (*C. trachomatis, C. pneumoniae, C. psittaci*); *Chlamydophila* spp. (*C. pneumoniae*); *Citrobacter* spp.; *Coxiella* spp. (*C. burnetti*); *Edwardsiella* spp.; *Enterobacter* spp.; *Ehrlichia* spp. (*E. canis, E. chaffeensis*); *Escherichia* spp. (*E. coli*); *Francisella* spp. (*F. tularensis*); *Gardnerella* spp.; *Haemophilus* spp. (*H. influenzae*); *Helicobacter* spp. (*H. pylori*); *Klebsiella* spp. (*K. pneumoniae*); *Legionella* spp. (*L. pneumophila*); *Leptospira* spp. (*L. interrogans*); *Moraxella* spp. (*M. catarrhalis*); *Mycoplasma* spp. (*M. pneumoniae*); *Neisseria* spp. (*N. gonorrhoeae, N. meningitidis*); *Pasteurella* spp.; *Proteus* spp.; *Providencia* app.; *Pseudomonas* spp. (*P. aeruginosa, P. mallei*); *Rickettsia* spp. (*R. akari, R. prowazekii, R. rickettsia*); *Salmonella* spp. (*S. enterica, S. enterica enteritidis, S. enterica hadar, S. enterica* Heidelberg, *S. enterica infantis, S. enterica paratyphi, S. enterica typhi, S. enterica typhimurium*); *Serratia* spp.; *Shigella* spp. (*S. dysenteriae, S. sonnei*); *Spirillaceae* spp. (*S. minus*); *Streptobacillus* spp. (*S. moniliformis*); *Treponema* spp. (*T. pallidum*); *Vibrio* spp. (*V. cholerae*); and *Yersinia* spp. (*Y. enterocolitica, Y. pestis, Y. pseudotuberculosis*), or combinations thereof.

Gram-positive bacteria include, for example, *Actinomyces* spp. (*A. israelii*); *Aerococcus* spp.; *Bacillus* spp. (*B. anthracis*); *Bacterionema* spp.; *Bifidobacterium* spp.; *Clostridium* spp. (*C. botulinum, C. difficile, C. perfringens, C. tetani*); *Corynebacterium* spp. (*C. diphtheriae*); *Corprococcus* spp.; *Deinobacter* spp.; *Deinococcus* spp.; *Enterococcus* spp. (*E. faecalis, E. faecium*); *Erysipelothrix* spp.; *Eubacterium* spp.; *Gemella* spp.; *Lactobacillus* spp.; *Lactococcus* spp.; *Leuconostoc* spp.; *Listeria* spp. (*L. monocytogenes*); *Marinococcus* spp.; *Melissococcus* spp.; *Methanobacterium* spp.; *Micrococcus* spp.; *Mycobacterium* spp. (*M. avium, M. leprae, M. lepromatosis, M. tuberculosis, M. ulcerans*); *Micropolyspora* spp.; *Nocardia* spp. (*N. asteroides*); *Pediococcus* spp.; *Peptococcus* spp.; *Peptostreptococcus* spp.; *Planococcus* spp.; *Propionibacterium* spp.; *Rothia* spp.; *Ruminococcus* spp.; *Saccharococcus* spp.; *Salinococcus* spp.; *Carcina* spp.; *Staphylococcus* spp. (*S. aureus, S. epidermidis, S. saprophyticus*); *Stomatococcus* spp.; *Streptococcus* spp. (*S. agalactiae, S. pneumoniae, S. pyogenes, S. viridans*); *Streptomyces* spp.; *Trichococcus* spp.; and *Vagococcus* spp, or combinations thereof.

Pathological conditions in humans caused by Gram-negative bacteria include, for example, pneumonia such as pneumococcal pneumonia, sepsis (caused by, for example, *N. meningitides, K. pneumoniae*), typhoid fever (caused by, for example, *Salmonella*), diphtheria (caused by, for example, *C. diphtheriae*), syphilis (caused by, for example, *T. palladium*), Q fever (caused by, for example, *C. burnetii*), Black Plague (caused by, for example, *Y. pestis*), Bubonic Plague (caused by, for example, *Y. pestis*), Pneumonic Plague (caused by, for example, *Y. pestis*), chlamydia (caused by, for example, *C. trachomatis*), gonorrhea (caused by, for example, *N. gonorrhoeae*), whooping cough (caused by, for example, *B. pertussis*), lyme disease (caused by, for example, *B. burgdorferi*), bacterial meningitis (caused by, for example, *H. influenzae*), Legionnaire's Disease (caused by, for example, *L. pneumophila*), Rocky Mountain Spotted Fever (caused by, for example, *R. rickettsia*), glanders (caused by, for example, *B. mallei*), and cholera (caused by, for example, *V. cholerae*).

Pathological conditions in humans caused by Gram-positive bacteria include, for example, local and systemic staphylococcal infections, toxic shock syndrome (caused by, for example, Staphylococcal), sepsis (caused by, for example, *Streptococcus, Staphylococcus*), erysipelas (caused by, for example, *Streptococcus*), scarlet fever (caused by, for example, *Streptococcus*), botulism (caused by, for example, *C. botulinum*), tetanus (caused by, for example, *C. tetani*), leprosy (caused by, for example, *M. leprae, M. lepromatosis*), impetigo (caused by, for example, *S. aureus, S. pyogenes*), actinomycosis (caused by, for example, *A. israelii*), anthrax (caused by, for example, *B. anthracis*), Buruli ulcer (caused by, for example, *M. ulcerans*), tuberculosis (cause by, for example, *M. tuberculosis*), and cellulitis (caused by, for example, *Streptococcus*).

Pathological conditions in humans caused by bacteria may further include, for example, osteomyelitis, pyoderma, bacterial vaginosis, urinary tract infection, brucellosis, dysentery, and bacterial gastroenteritis.

"Minimal inhibitory concentration" or "MIC" refers to the minimum concentration, usually in micrograms per milliliter, of an antimicrobial agent at which no microbial growth is observed. At concentrations below the MIC, the antimicrobial agent is ineffective at killing or inhibiting the growth and reproduction of microbes. At concentrations above the MIC, the antimicrobial agent is effective at killing or inhibiting the growth and reproduction of microbes.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Sample" or "test sample" as used herein can mean any sample in which the presence and/or level of a target or activity is to be detected or determined or any sample comprising an efflux pump or an inhibitor as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchioalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described inhibitors. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. The subject may be of any age or stage of development, such as, for example, an adult, an adolescent, a child, or an infant. In some embodiments, the subject is human. In some embodiments, the subject has a specific genetic marker.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

A "therapeutically effective amount" is an amount sufficient to elicit a therapeutic effect. Amounts effective for this use will depend on, e.g., the particular composition of the regimen administered, the manner of administration, the stage and severity of the disease or infection, the general state of health of the subject, and the judgment of the prescribing physician. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease or infection, the prophylactically effective amount will be less than the therapeutically effective amount.

"Toxic" refers to a substance causing any adverse effect when administered to a subject. The term "non-toxic" refers to a substance that has a relatively low degree to which it can damage a subject. Toxicity can refer to the effect on a whole organism, such as an animal, bacterium, plant, or other subject as defined herein, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom there is a dose below which there is no detectable toxic effect. A composition or inhibitor that is relatively non-toxic may allow a wider range of subjects to be able to safely handle the composition or inhibitor, without serious safety concerns or risks.

"Treatment" or "treating," when referring to protection of a subject from a disease or infection means preventing, suppressing, repressing, ameliorating, or completely eliminating the disease or infection. Preventing the disease or infection involves administering an inhibitor or composition of the present invention to a subject prior to onset of the disease or infection. Suppressing the disease or infection involves administering an inhibitor or composition of the present invention to a subject after induction of the disease or infection but before its clinical appearance. Repressing or ameliorating the disease or infection involves administering an inhibitor or composition of the present invention to a subject after clinical appearance of the disease or infection.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequence substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. EFFLUX PUMPS

Efflux pumps are complexes comprising polypeptides and are transporters for moving substances out of a cell. Efflux pumps are used by the cell to remove toxic substances from the intracellular environment before damage to the cell occurs. Substances that may be transported out of a cell by an efflux pump include, for example, toxic substances, neurotransmitters, acids such as bile acids and fatty acids, lipids, beta-lactams, fluoroquinolones, sodium dodecylsulfate (SDS), dyes such as ethidium bromide and crystal violet, homoserine lactones, and antibiotics. Efflux pumps are localized in the cytoplasmic membrane or envelope of a cell. Efflux pumps may be active transporters, wherein they require a source of chemical energy to perform their function. Active transporters include primary active transporters that use, for example, ATP hydrolysis as a source of energy. Active transporters also include secondary active transporters, wherein transport is coupled to an electrochemical potential difference created by pumping ions, such as hydrogen or sodium ions, from or to the outside of the cell. Efflux pumps may be specific, in that they transport a single substance or single type of substance, or efflux pumps may be general and transport multiple types of substances out of a cell. Efflux pump substrate recognition may be based on the substance's physicochemical properties, such as hydrophobicity, hydrophilicity, amphiphilicity, aromaticity, ionizable character, or a combination thereof. Different efflux pumps may have similar or overlapping substrate specificities.

Efflux pumps may be encoded, for example, by a cell's chromosomes or a transportable genetic element. Transportable genetic elements include, for example, plasmids and transposons. A cell may express several types of efflux pumps.

In some embodiments, the efflux pump is a bacterial efflux pump. Bacterial efflux pumps may be classified into five superfamilies, based on their amino acid sequence and the energy source used to transport the substance. The bacterial efflux pump superfamilies include the major facilitator family (MFS), ATP-binding cassette superfamily (ABC), small multidrug resistance family (SMR), resistance-nodulation-cell division superfamily (RND), and multi-antimicrobial extrusion protein family (MATE). The ABD superfamily are primary transporters. The MFS, SMR, RND, and MATE superfamilies are secondary transporters. The MFS, ABC, SMR, and MATE superfamilies are found in all bacteria. The RND superfamily is found only in Gram-negative bacteria. The MFS, ABC, SMR, and RND superfamilies may recognize substrates with polycationic properties. In some embodiments, the efflux pump is from the MFS superfamily. In some embodiments, the efflux pump is from the ABC superfamily. In some embodiments, the efflux pump is from the SMR superfamily. In some embodiments, the efflux pump is from the RND superfamily. In some embodiments, the efflux pump is from the MATE superfamily.

3. EFFLUX PUMP INHIBITORS

Provided herein are efflux pump inhibitors, which may also be referred to as efflux inhibitors. Efflux pump inhibitors may inhibit an efflux pump by direct inhibition. In such embodiments, the inhibitor may bind the binding site for the native substrate on the efflux pump. The inhibitor may bind an efflux pump directly. In some embodiments, the inhibitor binds an efflux pump with greater affinity than an antibiotic. In some embodiments, the inhibitor binds an efflux pump with less affinity than an antibiotic. In some embodiments, the inhibitor displaces an antibiotic from its binding site on an efflux pump. The inhibitor may displace at least 50%, at least 55%, at least 60%, at least 65%, at least 70%, at least 75%, at least 80%, at least 85%, at least 90%, or at least 95% of an antibiotic from its binding site on an efflux pump.

The efflux pump inhibitors detailed herein may inhibit bacterial efflux pumps. In some embodiments, the efflux pump inhibitors are specific for bacterial efflux pumps. In some embodiments, the efflux pump inhibitors do not inhibit efflux pumps from organisms other than bacteria. In some embodiments, the inhibitors inhibit efflux pumps in Gram-negative bacteria. In some embodiments, the inhibitors inhibit efflux pumps in Gram-positive bacteria. In some embodiments, the inhibitors inhibit efflux pumps in both Gram-negative and Gram-positive bacteria.

Efflux pumps may contribute to drug resistance. Efflux pumps may also contribute to multi-drug resistance. For example, in bacteria efflux pumps may contribute to multi-drug resistance because bacteria can include efflux pumps with a broad range of substrate specificities that encompass multiple antibiotic classes. Accordingly, in some embodiments, the inhibitors detailed herein prevent or decrease the rate of antibiotic resistance.

The inhibitor may increase the effectiveness of an antibiotic and reduce the amount of antibiotic that needs to be administered to a subject. In some embodiments, the inhibitors detailed herein reduce the therapeutic amount of an antibiotic. The inhibitor may reduce the therapeutic amount of an antibiotic by at least 2-fold, at least 3-fold, at least 4-fold, at least 5-fold, at least 6-fold, at least 7-fold, at least 8-fold, at least 9-fold, at least 10-fold, at least 15-fold, or at least 20-fold. In some embodiments, the inhibitors detailed herein reduce the minimum inhibitory concentration (MIC) of an antibiotic. The inhibitor may reduce the MIC by at least 2-fold, at least 3-fold, at least 4-fold, at least 5-fold, at least 6-fold, at least 7-fold, at least 8-fold, at least 9-fold, at least 10-fold, at least 15-fold, or at least 20-fold. In some embodiments, the efflux pump inhibitor is an adjuvant for an antibiotic.

In some embodiments, the inhibitors detailed herein do not have any off-target effects. In some embodiments, the inhibitors detailed herein are not antimicrobials. The inhibitors may not display any antimicrobial activity when administered on their own. In some embodiments, the inhibitors detailed herein do not have any deleterious effects on bacterial cell membranes. Deleterious effects on bacterial cell membranes include depolarizing the bacterial cell membrane, leading to cell death. In some embodiments, the inhibitors detailed herein are not toxic to mammalian cells. In some embodiments, the inhibitors do not inhibit mammalian efflux pumps. In some embodiments, the inhibitors do not inhibit mammalian ion channels such as calcium ion channels.

The activity of the inhibitor may be examined by any suitable means known in the art. For example, the activity of the inhibitor may be examined by measuring the capacity of the inhibitor to inhibit the transport of ethidium bromide from cells such as bacterial cells. The activity of the inhibitor may be examined by measuring the capacity of the inhibitor to inhibit the transport of labelled molecules from cells. Suitable labels are known in the art and include, for example, radiolabels and fluorescent labels. The activity of the inhibitor may be determined by examining cell growth before and after administration of the inhibitor.

4. COMPOUNDS

The efflux pump inhibitor may be a compound according to Formula I:

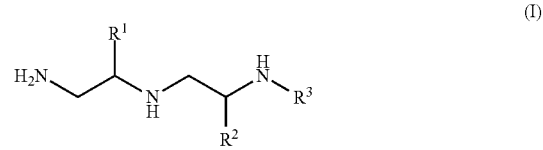

(I)

or a pharmaceutically acceptable salt thereof,
wherein $R^1$ is —$(CH_2)_n$—Y,
Y is methyl, —NH—X, cycloalkyl, aryl, or heteroaryl,
X is H or methyl,
n is an integer from 0 to 10,
$R^2$ is —$(CH_2)_m$—Z,
Z is cycloalkyl, aryl, heteroaryl, or amino,
m is an integer from 0 to 5,
$R^3$ is —$(CH_2)_p$-Q,
Q is cycloalkyl, aryl, heteroaryl, or amino,
p is an integer from 0 to 5.

In some embodiments of Formula I, Y is —NH—X, wherein X is methyl. In some embodiments, Y is —NH—X, wherein X is H. In some embodiments, Y is aryl. In some embodiments, Y is phenyl. In some embodiments, Z is aryl. In some embodiments, Z is phenyl. In some embodiments, Z is amino. In some embodiments, Q is aryl. In some embodiments, Q is phenyl.

In some embodiments of Formula I, $R^1$ is —$(CH_2)_n$—Y, Y is —NH—X, X is methyl, n is 4, $R^2$ is —$(CH_2)_m$—Z wherein Z is phenyl and m is 1, and $R^3$ is —$(CH_2)_p$-Q wherein Q is phenyl and p is 2.

In some embodiments of Formula I, $R^1$ is —$(CH_2)_n$—Y, Y is —NH—X, X is H, n is 2, $R^2$ is —$(CH_2)_m$—Z wherein Z is phenyl and m is 1, and $R^3$ is —$(CH_2)_p$-Q wherein Q is phenyl and p is 2.

In some embodiments of Formula I, $R^1$ is —$(CH_2)_n$—Y, Y is —NH—X, X is methyl, n is 4, $R^2$ is —$(CH_2)_m$—Z wherein Z is phenyl and m is 1, and $R^3$ is —$(CH_2)_p$-Q wherein Q is phenyl and p is 2.

In some embodiments of Formula I, $R^1$ is —$(CH_2)_n$—Y, Y is —NH—X, X is H, n is 3, $R^2$ is —$(CH_2)_m$—Z wherein Z is phenyl and m is 1, and $R^3$ is —$(CH_2)_p$-Q wherein Q is phenyl and p is 2.

In some embodiments of Formula I, $R^1$ is —$(CH_2)_n$—Y, Y is phenyl, n is 1, $R^2$ is —$(CH_2)_m$—Z wherein Z is amino and m is 3, and $R^3$ is —$(CH_2)_p$-Q wherein Q is phenyl and p is 2.

The efflux pump inhibitor may be a compound according to Formula Ia:

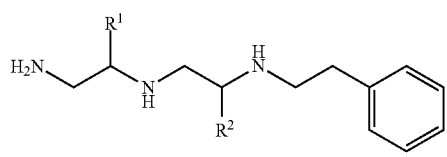

(Ia)

or a pharmaceutically acceptable salt thereof,
wherein $R^1$ is —$(CH_2)_n$—Y;
Y is methyl, —NH—X, cycloalkyl, aryl, or heteroaryl;
X is H or methyl;
n is an integer from 0 to 10;
$R^2$ is —$(CH_2)_m$—Z;
Z is cycloalkyl, aryl, heteroaryl, or amino; and
m is an integer from 0 to 5.

In some embodiments of Formula Ia, Y is —NH—X, wherein X is methyl. In some embodiments, Y is —NH—X, wherein X is H. In some embodiments, Y is aryl. In some embodiments, Y is phenyl. In some embodiments, Z is aryl. In some embodiments, Z is phenyl. In some embodiments, Z is amino.

In some embodiments of Formula Ia, $R^1$ is —$(CH_2)_n$—Y, Y is —NH—X, X is methyl, n is 4, and $R^2$ is —$(CH_2)_m$—Z wherein Z is phenyl and m is 1.

In some embodiments of Formula Ia, $R^1$ is —$(CH_2)_n$—Y, Y is —NH—X, X is H, n is 2, and $R^2$ is —$(CH_2)_m$—Z wherein Z is phenyl and m is 1.

In some embodiments of Formula Ia, $R^1$ is —$(CH_2)_n$—Y, Y is —NH—X, X is methyl, n is 4, and $R^2$ is —$(CH_2)_m$—Z wherein Z is phenyl and m is 1.

In some embodiments of Formula Ia, $R^1$ is —$(CH_2)_n$—Y, Y is —NH—X, X is H, n is 3, and $R^2$ is —$(CH_2)_m$—Z wherein Z is phenyl and m is 1.

In some embodiments of Formula Ia, $R^1$ is —$(CH_2)_n$—Y, Y is phenyl, n is 1, and $R^2$ is —$(CH_2)_m$—Z wherein Z is amino and m is 3.

In some embodiments, the efflux pump inhibitor comprises one of the following compounds:

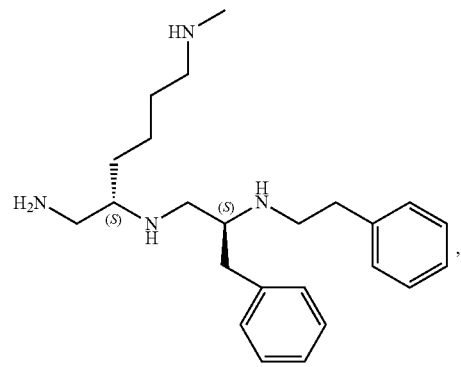

247

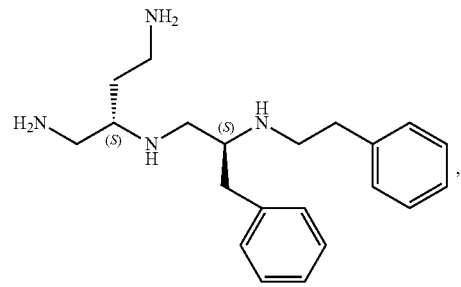

250

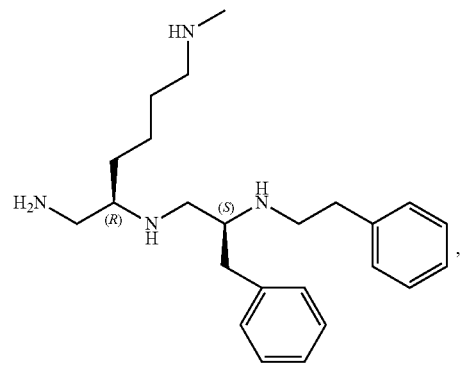

266

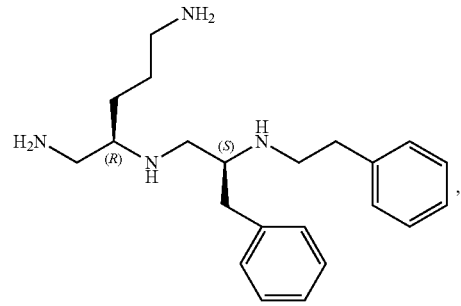

271

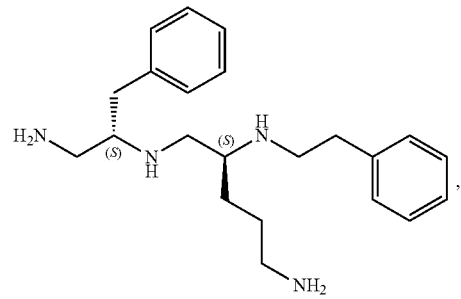

314 or a pharmaceutically acceptable salt thereof.

The compound, or a pharmaceutically acceptable salt thereof, may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45, 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

In some embodiments of Formula I or Ia, the carbon atom to which $R^1$ is attached has (S) configuration. In some embodiments, the carbon atom to which $R^1$ is attached has (R) configuration. In some embodiments, the carbon atom to which $R^2$ is attached has (S) configuration. In some embodiments, the carbon atom to which $R^2$ is attached has (R) configuration. In some embodiments, the carbon atom to which $R^1$ is attached has (S) configuration, and the carbon atom to which $R^2$ is attached has (S) configuration. In some embodiments, the carbon atom to which $R^1$ is attached has (R) configuration, and the carbon atom to which $R^2$ is attached has (S) configuration.

It should be understood that the compound may possess tautomeric forms, as well as geometric isomers, and that these also constitute embodiments of the disclosure.

The present disclosure also includes an isotopically-labeled compound, which is identical to those recited in Formulas I and Ia, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of Formulas I and Ia are $^{11}C$, $^{13}N$, $^{15}O$, and $^{18}F$. Isotopically-labeled compounds of Formulas I and Ia can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. Synthesis of Compounds

Figure 9:
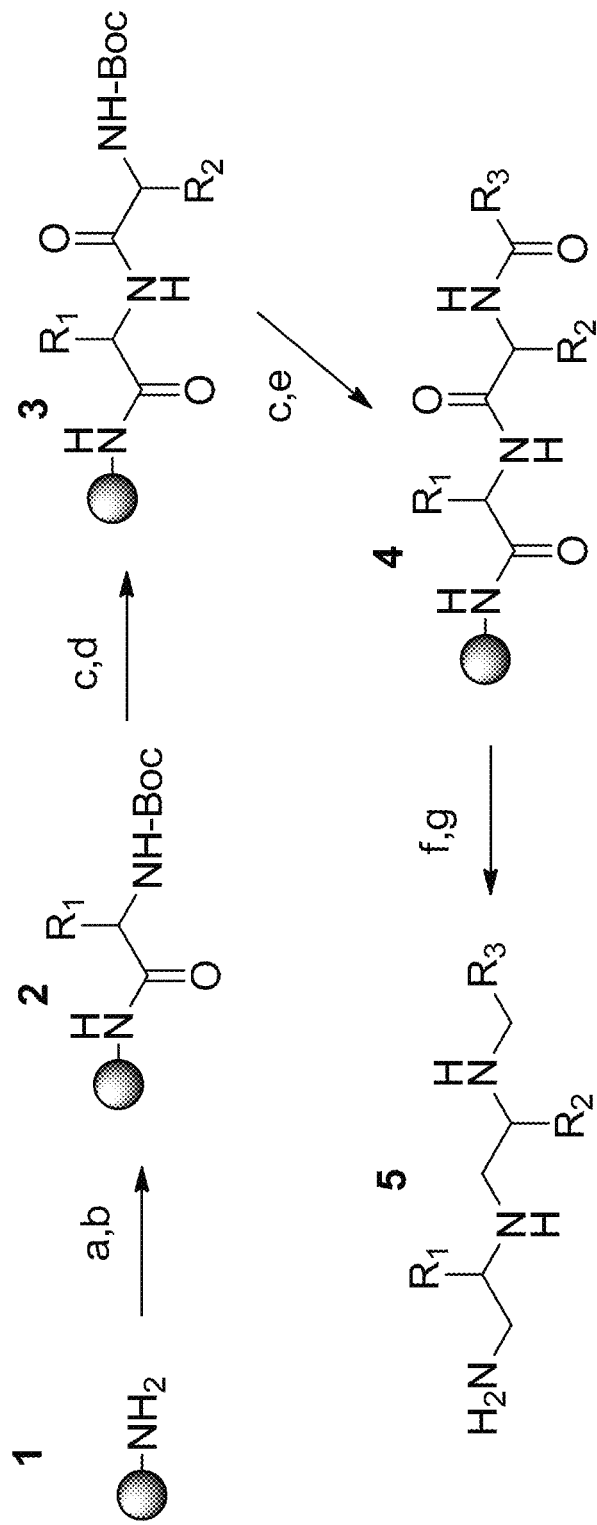
FIG. 9 is a Synthetic Scheme of Polyamines. a, 5% DIEA/DCM; b, Boc-AA(R$_1$), DIC, HOBt, DMF; c, 55% TFA/DCM; 5% DIEA/DCM; d, Boc-AA(R$_2$), DIC, HOBt, DMF; e, R$_3$COOH, DIC, HOBt, DMF; f, BH$_3$-THF, 65° C., 96 hours; Piperidine, 65° C., 24 hours; g, HF, anisole, 0° C.

The compounds as detailed herein may be synthesized as detailed in FIG. 9 and Example 2. Alternatively, the compounds as detailed herein may be synthetically made by methods known to one of skill in the art.

c. Pharmaceutical Compositions

The efflux pump inhibitors as detailed herein may be formulated into pharmaceutical compositions accordance with standard techniques well known to those skilled in the pharmaceutical art. The composition may comprise at least one efflux pump inhibitor in combination with at least one antibiotic. The composition may comprise the compound and a pharmaceutically acceptable carrier. The term "pharmaceutically acceptable carrier," as used herein, means a non-toxic, inert solid, semi-solid or liquid filler, diluent, encapsulating material or formulation auxiliary of any type.

The route by which the disclosed efflux pump inhibitors are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). In some embodiments, the pharmaceutical composition is for administration to a subject's central nervous system. Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 0.1 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, Pa.) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate. In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include an efflux pump inhibitor (e.g., a compound of Formula I or Ia), and a carrier including one or more diluents disclosed above in a capsule comprising gelatin. Granules typically comprise an efflux pump inhibitor, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a disclosed efflux pump inhibitor is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include an efflux pump inhibitor and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the efflux pump inhibitors into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of an efflux inhibitor (e.g., a compound of Formula I or Ia) and 50% to 99.99% of one or more carriers. Compositions for parenteral administration may typically include 0.1% to 10% of an efflux pump inhibitor and 90% to 99.9% of one or more carriers. Oral dosage forms may include, for example, at least about 5%, or about 25% to about 50% of an efflux pump inhibitor. The oral dosage compositions may include about 50% to about 95% of carriers, or from about 50% to about 75% of carriers. The amount of the carrier employed in conjunction with a disclosed efflux pump inhibitor is sufficient to provide a practical quantity of composition for administration per unit dose of the efflux pump inhibitor. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

d. Administration

The efflux pump inhibitors as detailed herein, or the pharmaceutical compositions comprising the same, may be administered to a subject. Such compositions comprising an efflux pump inhibitor can be administered in dosages and by techniques well known to those skilled in the medical arts taking into consideration such factors as the age, sex, weight, and condition of the particular subject, and the route of administration.

The efflux pump inhibitor can be administered prophylactically or therapeutically. In prophylactic administration, the efflux pump inhibitor can be administered in an amount sufficient to induce a response. In therapeutic applications, the efflux pump inhibitors are administered to a subject in need thereof in an amount sufficient to elicit a therapeutic effect. The efflux pump inhibitor may be administered in a therapeutically effective amount.

For example, a therapeutically effective amount of a compound of Formula I or Ia or a pharmaceutically acceptable salt thereof, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The efflux pump inhibitor can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The efflux pump inhibitor can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The efflux pump inhibitor can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the efflux pump inhibitor is administered intravenously, intraarterially, or intraperitoneally to the subject. In some embodiments, the efflux pump inhibitor is administered to the subject orally.

In some embodiments, the inhibitor is co-administered with at least one antibiotic.

5. METHODS a. Methods of Preventing Antibiotic Resistance

Provided herein are methods of preventing antibiotic resistance in a subject. The method may include administering to the subject an efflux pump inhibitor as detailed herein. In some embodiments, the inhibitor is co-administered with at least one antibiotic.

b. Methods of Treating a Bacterial Infection

Provided herein are methods of treating a bacterial infection in a subject. The bacterial infection may be any pathological condition caused by bacteria. The method may include administering to the subject an efflux pump inhibitor as detailed herein. In some embodiments, the inhibitor is co-administered with at least one antibiotic.

6. EXAMPLES

Example 1

Materials and Methods

Torrey Pines Scaffold Ranking Library.

The design and synthesis of the Torrey Pines scaffold ranking library has previously been described (Houghten, et al. *J. Med. Chem.* 1999, 42, 3743-3778; Reilley, et al. *AAPS J.* 2010, 12, 318-329; Santos, et al. *Molecules* 2013, 18, 6408-6424; Wu, et al. *J. Med. Chem.* 2013, 56, 10103-10117). The library is comprised of 84 different scaffolds, each with 10,000-750,000 compounds, in approximately equal molar amounts. The polyamine library chosen for analysis contains 399,766 analogs; from this, 188 individual compounds were chosen for analysis. Detailed chemical characterization for scaffold libraries and individual compounds can be found Example 2. Individual compounds were synthesized as described in Example 2.

Bacterial Strains and Growth Conditions.

The bacterial strains used in this study are multi-drug resistant clinical isolates that have previously been described (TABLE 2) (Fleeman, et al. *J. Med. Chem.* 2015, 58, 3340-3355). Organisms were grown in tryptic soy broth (TSB) for overnight cultures, and cation adjusted Mueller Hinton broth (CA-MH II) was used for experimental procedures. All incubations were performed at 37° C.

TABLE 2

Clinical isolates used in this study.

| Strain Name | Identifying Features* | References |
|---|---|---|
| *S. aureus* | | |
| 635 | R = Ampicillin, Azithromycin, Chloramphenicol, Clindamycin, Cathomycin, Erythromycin, Penicillin S = Gentamycin, Oxacillin, Sulfamethoxazole, Rifampin, Tetracycline | Carroll, et al. *Genome Announc.* 2013, 1, e00491-13. |
| *A. baumannii* | | |
| 1403 | R = Ampicillin, Ciprofloxacin, Gentamycin, Polymyxin B, Trimethoprim, Sulfamethoxazole, Tetracycline S = Rifampin, Chloramphenicol, Imipenem | Fleeman, et al. *J. Med. Chem.* 2015, 58, 3340-3355. |
| *P. aeruginosa* | | |
| 1419 | R = Ampicillin, Polymyxin B, Gentamycin, Chloramphenicol, Imipenem, Tetracycline S = Ciprofloxacin | Fleeman, et al. *J. Med. Chem.* 2015, 58, 3340-3355. |

*Identifying features: resistance (R) and susceptibility (S) towards common clinical antibiotic agents, where resistance is defined as minimal inhibitory concentration >5 µg mL$^{-1}$.

Checkerboard Potentiation Assays.

Scaffold ranking library samples and individual polyamines were screened using checkerboard inhibitory assays to assess the potentiation of tetracycline and chloramphenicol. The test utilized a 96-well plate microtiter assay where the concentration of the scaffold or individual polyamine was decreased from 25 µg mL$^{-1}$ to 0.8 µg mL$^{-1}$ (average molarity of 65 µM to 4 µM) along the rows, and the concentration of tetracycline or chloramphenicol was increased from 0.4 µM to 100 µM across the columns. Plates were incubated statically at 37° C. for 20 hours, and the optical density (OD$_{600}$) was determined using a Synergy 2 plate reader (Biotek). Potentiation modeling (detailed below) was performed to determine fold change in the 50% and 90% effective concentration of tetracycline or chloramphenicol.

Statistical Analysis of Checkerboard Assays.

Potentiation was quantified using a mathematical model developed by our group to assess the ability of library samples and individual compounds to effectively enhance the activity of tetracycline or chloramphenicol (Hoel, D. G. *Statistical Aspects of Chemical Mixtures. Methods for assessing the effects of mixtures of chemicals.* 1987, New York). This was used to differentiate libraries or compounds that possessed only antibacterial activity from those that had synergistic activity with tetracycline or chloramphenicol. In this way, only libraries and compounds that potentiated tetracycline or chloramphenicol activity were pursued. The model is based on the following equation for modeling the percentage activity of a mixture of two agents with independent action (Hoel, et al. Statistical Aspects of Chemical Mixtures. Methods for assessing the effects of mixtures of chemicals. 1987, New York):

$$\%_{Antibiotic\ \&\ Comp}(x_1, x_2) = \%_{Antibiotic}(x_1) + \%_{Comp}(x_2) - \%_{Antibiotic}(x_1) \cdot \%_{Comp}(x_2)$$

Here, $x_1$ and $x_2$ are the concentrations of antibiotic (tetracycline or chloramphenicol) and library/compound (Comp) tested, respectively. This equation can be rearranged to model the effective percent activity (EC) of the antibiotic alone, after accounting for compound activity:

$$Eff\ \%_{Antibiotic}(x_1) = \frac{\%_{Antibiotic\ \&\ Compound}(x_1, x_2) - \%_{Compound}(x_2)}{1 - \%_{Compound}(x_2)}$$

Thus, the model-adjusted checkerboards show the antibiotic activity post-potentiation, and from that one can determine the true change in MIC.

Ethidium Bromide Efflux Inhibition Assay.

Ethidium bromide efflux assessment was performed by following the fluorescence of ethidium bromide in a 96-well plate assay, as described previously (Renau, et al. *J. Med. Chem.* 1999, 42, 4928-4931; Lomovskaya, et al. *Antimicrobial Agents and Chemotherapy* 2001, 45, 105-116; Webber, et al. *PLoS One* 2013, 8, e60666; Blanchard, et al. *Antimicrobial Agents and Chemotherapy* 2014, 58, 11, 6360-6370; Vasudevan et al. *International Journal of Pharmacy and Pharmaceutical Sciences* 2014, 6, 84-89). Bacterial cells were grown overnight at 37° C. in TSB, before being synchronized for three hours in fresh media to exponential phase. Cultures were pelleted at 900×G for 20 mins and the supernatant removed. The resulting pellet was thrice washed, and resuspended in 20 mM sodium phosphate buffer to an $OD_{600}$ of 0.2. Ethidium bromide was next added at a sub inhibitory concentration of 25 µM and incubated at room temperature for 15 minutes to equilibrate. After equilibration, cells were inoculated into a black walled 96-well plate to a density of $1\times10^6$ CFU $mL^{-1}$. Using a Biotek plate reader, the fluorescence of cells was monitored for 2 minutes with 530 nm excitation and 600 nm emission. When baseline readings were complete, polyamines 247, 250, 266, 271, and 314 were added at 25 µg $mL^{-1}$ alongside the positive control PaβN at the same concentration (all EPI concentrations were maximum potentiating concentrations (MPC)). The solvent DMF was used as a no treatment control alongside tetracycline alone. After addition of all compounds, fluorescence was monitored every five minutes for a total of 90 minutes. After this time, cells were serially diluted and plated to ensure that treatment with ethidium bromide did not affect viability. For graphical representation, the final maximum relative fluorescence at 90 minutes was used for comparison of lead agents to controls.

Bacterial Membrane Depolarization.

To determine the level of membrane depolarization by polyamine compounds a 3,3'-dipropylthiadicarbocyanine Iodide ($DiSC_3$) fluorescence dye was used. Exponentially growing cultures were prepared as described above, before being harvested by centrifugation. Cells were next washed in buffer A (5 mM HEPES pH 7.2, 5 mM glucose) and resuspended to an $OD_{600}$ of 0.2 in the same buffer containing 100 mM KCl and 2 µM $DiSC_3$. Samples were allowed to equilibrate for 15 minutes at room temperature to ensure uptake and quenching of the dye in bacterial membranes. Cells were aliquoted into 96-well plates and polyamines were added alongside the known efflux inhibitor PAN (all at 25 µg $mL^{-1}$). Nisin (25 µg $mL^{-1}$) was used as a positive control to display depolarization effects. A Biotek plate reader was used to monitor fluorescence of wells, with a 622 nm excitation and 670 nm emission. For graphical representation, the maximum relative fluorescence at 2 minutes was used for comparison of lead agents to controls.

Eukaryotic Cell Cytotoxicity.

To assess toxicity of polyamine compounds we used HepG2 human liver carcinoma cells and Hek293T human embryonic kidney epithelial cells. The viability of cell lines was determined using a 3-(4,5-Dimethylthiazol-2-Yl)-2,5-Diphenyltetrazolum Bromide (MTT) molecular probe as previously described (Fleeman, et al. *J. Med. Chem.* 2015, 58, 3340-3355). Briefly, 247, 266, 271 (Hek293T), or 250, 271, 314 (HepG2), alongside control EPI PaβN, were diluted in 10% DMF from 25 µg $mL^{-1}$ to 3 µg $mL^{-1}$ using 2-fold dilutions, before being added to cells in DMEM with 10% FBS and 1% penicillin/streptomycin. Cells were then incubated for 48 hours at 37° C. with 5% $CO_2$. Following this, viability was assessed by the addition of MTT and measuring the $OD_{570}$ in a Biotek plate reader. Percent recovery was determined compared to no drug controls.

Eukaryotic Calcium Channel Activity Assay.

The effects of polyamine efflux inhibitors on eukaryotic ion channels was performed using a calcium channel assay kit (Life Technologies, Brown Deer, Wis.) and the Hek293T kidney cell line. Cells ($5\times10^4$) were inoculated into a black walled 96-well plate and allowed to attach overnight at 37° C. with 5% $CO_2$. After this, the Fluo-4 dye supplemented with Probenecid (5 mM) was added and allowed to equilibrate for one hour at 37° C. with 5% $CO_2$. After this time, fluorescence was measured for 120 seconds using a Biotek plate reader with a 495 nm excitation and 516 nm emission. Cells were then treated with solvent only controls (10% DMF), as well as polyamine compounds 250, 266, 271, and the known calcium channel inhibitor verapamil (all at 25 µg $mL^1$). Fluorescence was monitored for 120 seconds, before calcium channels were stimulated with carbamylcholine chloride (137 µM). Readings were then taken at 6 second intervals, with peak relative fluorescence at 18 seconds used graphically for comparison of lead agents to controls.

Bactericidal and Biofilm Assessment.

Lead agents were screened for bactericidal activity as described previously (Van Horn, et al. *J. Med. Chem.* 2014, 57, 3075-3093; Fleeman, et al. *J. Med. Chem.* 2015, 58, 3340-3355), with the following modifications. Varying concentrations of tetracycline (0, 12, 25, and 50 µM) were used in combination with the MPC (25 µM) of lead agents 247, 250, 266, 271, and 314 against *P. aeruginosa*. Data is shown as percent recovery by dividing the CFU $mL^1$ of treatment groups by the CFU $mL^1$ recovered from a no treatment control that did not have tetracycline or efflux inhibitors. Biofilm experiments were performed similar to those described previously (Fleeman, et al. *J. Med. Chem.* 2015, 58, 3340-3355; von Salm, et al. *Org. Lett.* 2016, 18, 2596-2599), with the following modifications. Polyamine agents 247, 250, 266, 271, and 314 were added at MPC into biofilm containing wells alongside varying concentrations of tetracycline (0, 12, 25, and 50 µM). Cellular viability was determined by serial dilution after a 20-hour incubation at 37° C. Values were converted to percent recovery using no treatment controls. All data was generated from three biological replicates and two technical replicates.

Example 2

Synthesis of Compounds

Synthesis of Library 2229 and Individual Compounds and Construction of Scaffold Ranking Plate.

Library 2229 as well as the individual compounds reported herein (247, 250, 266, 271, and 314) were synthesized following the same synthetic scheme (FIG. 9) as previously reported (Nefzi, et al. *J. Comb. Chem.* 2001, 3, 68-70; Nefzi, et al. *Chem. Rev.* 1997, 97, 449-472; Sandhaus, et al. *Antimicrobial Agents and Chemotherapy* 2016, 60, 4028-4036). Utilizing the "tea-bag" methodology (Houghten, et al. *PNAS* 1985, 82, 5131-5135), 100 mg of p-methylbenzhydrylamine (MBHA) resin (1.1 mmol/g, 100-200 mesh) was sealed in a mesh "tea-bag", neutralized with 5% diisopropylethylamine (DIEA) in dichloromethane (DCM) and subsequently swelled with additional DCM washes. Boc-Amino Acids ($R_1$) were coupled in Dimethylformamide (0.1 M DMF) for 120 mins in the presence of Diisopropylcarbodiimide (DIC, 6 equiv.) and 1-Hydroxybenzotriazole hydrate (HOBt, 6 equiv.) (Step 1, FIG. 9). The Boc protecting group was then removed with Trifluoroacetic Acid (TFA) in DCM for 30 mins and subsequently neutralized with 5% DIEA/DCM (3×). Boc-Amino Acids ($R_2$) were coupled utilizing standard coupling procedures (6 equiv.) with DIC (6 equiv.) and HOBt (6 equiv.) in DMF (0.1 M) for 120 mins. The Boc group was removed with 55% TFA/DCM for 30 mins and subsequently neutralized with 5% DIEA/DCM (3×). Carboxylic acids ($R_3$) were coupled using (10 equiv.) in the presence of DIC (10 equiv.) and HOBt (10 equiv.) in DMF (0.1 M) for 120 mins (Step 3, FIG. 9). All coupling reactions were monitored for completion using Ninhydrin. The reduction was performed in a 4000 mL Wilmad LabGlass vessel under nitrogen. 1.0 M Tetrahydrofuran (THF) borane complex solution was used in 40-fold excess for each amide bond. The vessel was heated to 65° C. and maintained at this temperature for 96 hrs. The solution was then removed and the bags were washed with THF and methanol (MeOH). Once completely dry, the bags were treated overnight with piperidine at 65° C. and washed several times with DMF, DCM, and methanol. As previously reported by our group and others, the reduction of polyamides with borane is free of racemization (Ostresh, et al. *J. Org. Chem.* 1998, 63, 8622-8623; Nefzi, et al. *Tetrahedron* 1999, 55, 335-344; Manku, et al. *J. Org. Chem.* 2001, 66, 874-885). Completion of reduction was monitored by LCMS analysis of a control compound that was cleaved from the solid support (HF, anisole, 0° C. 7 hours). The resin was cleaved with HF in the presence of anisole in an ice bath at 0° C. for 7 hours. After removal of the HF by gaseous $N_2$, the products were then extracted from the vessels with 95% acetic acid in water, transferred to scintillation vials, frozen and lyophilized. The compounds were then reconstituted in 50% acetonitrile and water, frozen and lyophilized three more times.

HPLC Purification and NMR (247, 250, 266, 271, and 314).

As previously reported (Sandhaus, et al. *Antimicrobial Agents and Chemotherapy* 2016, 60, 4028-4036) all purifications were performed on a Shimadzu Prominence preparative HPLC system, consisting of LC-8A binary solvent pump, a SCL-10A system controller, a SIL-10AP autosampler, and a FRC-10A fraction collector. A Shimadzu SPD-20A UV detector was used for detection. The wavelength was set at 214 nm during analysis. Chromatographic separations were obtained using a Phenomenex Luna C18 preparative column (5 µm, 150×21.5 mm i.d.) preceded by a Phenomenex C18 column guard (5 µm, 15×21.2 mm i.d.). Prominence prep software was used to set all detection and collection parameters. The mobile phases for HPLC purification were HPLC grade obtained from Sigma Aldrich (St. Louis, Mo.) and Fisher Scientific (Hampton, N.H.). The mobile phase consisted of a mixture of Acetonitrile/water (both with 0.1% formic acid). The initial setting for separation was set at 2% (v/v) Acetonitrile, which was held for 2 mins and the gradient was linearly increased to 20% (v/v) Acetonitrile over 4 mins. The gradient was then linearly increased to 55% (v/v) Acetonitrile over 36 mins. The HPLC system was set to automatically flush and re-equilibrate the column after each run for a total of 4 column volumes. The total flow rate was set to 12 mL/min and the total injection volume was set to 3900 µL. The fraction collector was set to collect from 6 to 40 mins. The corresponding fractions were then combined and lyophilized. The 1H spectra were obtained utilizing the Bruker 400 Ascend (400 MHz). NMR chemical shifts were reported in δ (ppm) using the δ 7.26 signal of CDCl3 (1H NMR).

LCMS Analysis.

As previously reported (Sandhaus, et al. *Antimicrobial Agents and Chemotherapy* 2016, 60, 4028-4036) the purity and identity of all individual compounds was verified using a Shimadzu 2010 LCMS system, consisting of a LC-20AD binary solvent pump, a DGU-20A degasser unit, a CTO-20A column oven, and a SIL-20A HT autosampler. A Shimadzu SPD-M20A diode array detector was used for detection. A full spectra range of 190-600 nm was obtained during analysis. Chromatographic separations were obtained using a Phenomenex GeminiC18 analytical column (5 µm, 50×4.6 mm i.d.) preceded by a Phenomenex C18 column guard (5 µm, 4×3.0 mm i.d.). All equipment was controlled and integrated by Shimadzu LCMS solutions software version 3. Mobile phases for LCMS analysis were HPLC grade or LCMS grade obtained from Sigma Aldrich (St. Louis, Mo.) and Fisher Scientific (Hampton, N.H.). The mobile phases consisted of a mixture LCMS grade Acetonitrile/water (both with 0.1% trifluoroacetic acid for a pH of 2.7). The initial setting for analysis was set at 5% Acetonitrile (v/v), and then was linearly increased to 95% Acetonitrile over 6 mins. The gradient was then held at 95% Acetonitrile for 2 mins, linearly decreased to 5% over 0.10 mins and held for an additional 1.90 mins. The total run time was equal to 12 mins. The total flow rate was set to 0.5 mL/minute. The column oven and flow cell temperature for the diode array detector was set at 30° C. The autosampler temperature was held at 15° C. 5 µL of compound was injected for analysis.

Chemical Synthesis of Individual Compounds (S)—N6-methyl-$N_2$—((S)-2-(phenethylamino)-3-phenylpropyl)hexane-1,2,6-triamine (247)

Using the synthetic approach described in FIG. 9 for the synthesis, 247 was synthesized using the following reagents:

Boc-L-Lysine(CIZ) (R1), Boc-L-Phenylalanine (R2), phenylacetic acid (R3). Final crude product was purified by HPLC as described above. 1H NMR (400 MHz, Deuterium Oxice): δ 7.44 (br. s., 5H) 7.34 (br. s., 5H) 3.40 (br. s., 3H) 3.16 (br. s., 1H) 3.06 (br.s., 3H) 2.94 (br. s., 3H) 2.78 (br. s., 2H) 2.71 (br. s., 4H) 1.62 (br. s., 3H) 1.26 (br. s., 3H). LCMS (ESI+) $C_{24}H_{38}N_4$ m/z 383.31 found [M+H]+: 383.20.

(S)—$N^2$—((S)-2-(phenethylamino)-3-phenylpropyl)butane-1,2,4-triamine (250)

Using the synthetic approach described in FIG. 9 for the synthesis, 250 was synthesized using the following reagents: Boc-L-Asparagine(Xan) (R1), Boc-L-Phenylalanine (R2), phenylacetic acid (R3). Final crude product was purified by HPLC as described above. 1H NMR (400 MHz, Deuterium Oxide): 8 ppm 7.44 (br. s., 4H) 7.33 (br. s., 6H) 3.59-3.68 (m, 1H) 3.39 (br. s., 1H) 3.05 (br. s., 2H) 2.90-2.99 (m, 1H) 2.63-2.90 (m, 2H) 1.72-1.79 (m, 2H) 1.63-1.95 (m, 1H). LCMS (ESI+) calculated for $C_{21}H_{32}N_4$ m/z 341.28 found [M+H]+: 341.15.

(R)—$N^6$-methyl-$N^2$—((S)-2-(phenethylamino)-3-phenylpropyl)hexane-1,2,6-triamine (266)

Using the synthetic approach described in FIG. 9 for the synthesis, 266 was synthesized using the following reagents: Boc-D-Lysine(CIZ) (R1), Boc-L-Phenylalanine (R2), phenylacetic acid (R3). Final crude product was purified by HPLC as described above. 1H NMR (400 MHz, Deuterium Oxide): δ. 7.37-7.54 (m, 6H) 7.31 (br. s., 4H) 3.40 (br. s., 2H) 2.95-3.07 (m, 6H) 2.90 (dd, J=13.27, 7.15 Hz, 1H) 2.71 (br. s., 4H) 1.64 (br. s., 2H) 1.31 (br. s., 1H). LCMS (ESI+) calculated for $C_{24}H_{38}N_4$ m/z 383.31 found [M+H]+: 383.20.

(R)—$N^2$—((S)-2-(phenethylamino)-3-phenylpropyl)pentane-1,2,5-triamine (271)

Using the synthetic approach described in FIG. 9 for the synthesis, 271 was synthesized using the following reagents: Boc-L-Glutamine(Xan) (R1), Boc-L-Phenylalanine (R2), phenylacetic acid (R3). Final crude product was purified by HPLC as described above. 1H NMR (400 MHz, Deuterium Oxide): δ 7.36-7.57 (m, 6H) 7.32 (br. s., 4H) 3.57 (br. s., 1H) 3.40 (br.s., 2H) 3.08-3.20 (m, 3H) 3.05 (br. s., 2H) 2.77 (br. s., 1H) 1.62 (br.s., 1H). LCMS (ESI+) calculated for $C_{22}H_{34}N_4$ m/z 354.28 found [M+H]+: 355.20.

(S)—$N^1$—((S)-1-amino-3-phenylpropan-2-yl)-$N^2$-phenethylpentane-1,2,5-triamine (314)

Using the synthetic approach described in FIG. 9 for the synthesis, 314 was synthesized using the following reagents: Boc-L-Phenylalanine (R1), Boc-L-Glutamine(Xan) (R2), phenylacetic acid (R3). Final crude product was purified by HPLC as described above. 1H NMR (400 MHz, Deuterium Oxide): δ. 7.44 (br. s., 4H) 7.28-7.39 (m, 6H) 3.29 (d, J=6.24 Hz, 1H) 3.08 (d, J=12.84 Hz, 3H) 3.00 (br. s., 4H) 2.75-2.95 (m, 4H) 1.66 (d, J=7.70 Hz, 2H) LCMS (ESI+) calculated for $C_{22}H_{34}N_4$ m/z 355.28 found [M+H]+: 355.20.

Example 3

Scaffold Ranking Library

We have previously described the synthesis and antibacterial activity of the Torrey Pines scaffold ranking library towards the ESKAPE pathogens. With the success of this screening, we decided to expand our approaches towards the development of anti-resistance agents, specifically targeting efflux mechanisms (Fleeman, et al. *J. Med. Chem.* 2015, 58, 3340-3355). As such, the 81 Torrey Pines scaffold samples were screened for their ability to decrease the 90% effective concentration ($EC_{90}$) of the known EP substrate, tetracycline, towards a tetracycline resistant strain of *P. aeruginosa* (tetracycline alone $EC_{90}$=82.5 µM). Upon analysis, 17 libraries resulted in a potentiated tetracycline $EC_{90}$ of 2-fold, whilst 6 resulted in a fold potentiation of 4 (FIG. 1, TABLE 3). A consideration with these studies is that we wish to identify EPIs, rather than compounds that have bacterial killing activity themselves. Upon testing the top 17 libraries we determined that 7 of them, including the 5 most active scaffolds, had individual antibacterial activity. Of the remaining 10 libraries, 2229 (polyamines derived from reduced acyl peptides) had the best potentiating effects (>4-fold, tetracycline $EC_{90}$ lowered to 21.03 µM), without itself having antibacterial activity. For this reason, we prioritized the 2229 polyamine scaffold for further assessment.

TABLE 3

Potentiation assessment of combinatorial scaffold libraries. All data pertains to 90% effective concentration (EC90), which is defined as a 90% decrease in the optical density values for cultures when read at 600 nm compared to untreated controls. The TPL column refers to the inhibitory concentration of the Torrey Pines Library alone (µg mL−1) to produce an EC90 value (note that 25 µg mL−1 was the highest concentration tested in these assays). TET + TPL displays the tetracycline concentration (µM) required to produce an EC90 in the presence of 25 µg mL−1 of each library. Fold Potentiation (FP) = EC90 tetracycline concentration with no TPL/EC90 tetracycline concentration with TPL. All assays were performed in triplicate alongside no drug controls, tetracycline alone controls (data not shown due to repetitive values, average concentration for EC90 across all replicates = 82.5 µM), as well as positive and negative controls (PaβN, 10% DMF).

| Library | TPL | TET + TPL | FP |
|---|---|---|---|
| 10% DMF | >25 | 47.58 | 1.33 |
| PAβn | >25 | 11.63 | 8.01 |
| 2408 | 7.67 | 3.20 | 25.63 |
| 2407 | 16.74 | 5.59 | 15.68 |
| 2353 | 15.73 | 5.93 | 14.75 |
| 2354 | 15.05 | 23.70 | 4.22 |
| 2157 | 16.15 | 20.13 | 4.19 |
| 2229 | >25 | 21.03 | 4.18 |
| 2355 | 15.17 | 23.70 | 3.89 |
| 1955 | >25 | 23.26 | 3.57 |
| 2356 | 14.37 | 21.53 | 2.79 |
| 1954 | >25 | 32.39 | 2.69 |
| 2161 | >25 | 38.32 | 2.36 |
| 2221 | >25 | 47.63 | 2.10 |
| 2048 | >25 | 47.78 | 2.09 |
| 2340 | >25 | 48.71 | 2.05 |
| 1275 | >25 | 48.94 | 2.04 |
| 2304 | >25 | 48.96 | 2.04 |
| 2222 | >25 | 44.76 | 2.03 |
| 2135 | >25 | 46.10 | 1.99 |
| 2225 | >25 | 46.53 | 1.99 |
| 2339 | >25 | 47.58 | 1.90 |
| 2291 | >25 | 49.74 | 1.89 |
| 2443 | >25 | 46.95 | 1.88 |
| 1952 | >25 | 45.08 | 1.88 |
| 1666 | >25 | 44.54 | 1.88 |
| 2220 | >25 | 49.22 | 1.86 |
| 2159 | >25 | 48.83 | 1.85 |
| 1509 | >25 | 49.11 | 1.83 |
| 1295 | >25 | 47.99 | 1.82 |
| 2344 | >25 | 49.95 | 1.80 |
| 2435 | >25 | 48.94 | 1.79 |
| 2228 | >25 | 49.86 | 1.79 |
| 2390 | >25 | 48.43 | 1.78 |
| 2227 | >25 | 46.61 | 1.78 |

TABLE 3-continued

Potentiation assessment of combinatorial scaffold libraries. All data pertains to 90% effective concentration (EC90), which is defined as a 90% decrease in the optical density values for cultures when read at 600 nm compared to untreated controls. The TPL column refers to the inhibitory concentration of the Torrey Pines Library alone (μg mL−1) to produce an EC90 value (note that 25 μg mL−1 was the highest concentration tested in these assays). TET + TPL displays the tetracycline concentration (μM) required to produce an EC90 in the presence of 25 μg mL−1 of each library. Fold Potentiation (FP) = EC90 tetracycline concentration with no TPL/EC90 tetracycline concentration with TPL. All assays were performed in triplicate alongside no drug controls, tetracycline alone controls (data not shown due to repetitive values, average concentration for EC90 across all replicates = 82.5 μM), as well as positive and negative controls (PaβN, 10% DMF).

| Library | TPL | TET + TPL | FP |
|---|---|---|---|
| 2439 | >25 | 47.84 | 1.76 |
| 1456 | >25 | 45.46 | 1.76 |
| 2160 | >25 | 48.13 | 1.76 |
| 2352 | >25 | 49.82 | 1.76 |
| 1953 | >25 | 48.71 | 1.75 |
| 2057 | >25 | 49.24 | 1.74 |
| 2058 | >25 | 48.45 | 1.74 |
| 2388 | >25 | 49.13 | 1.74 |
| 1988 | >25 | 48.48 | 1.73 |
| 1481 | >25 | 50.55 | 1.72 |
| 1409 | >25 | 49.04 | 1.71 |
| 1989 | >25 | 48.56 | 1.68 |
| 1983 | >25 | 48.27 | 1.66 |
| 2068 | >25 | 48.77 | 1.66 |
| 1984 | >25 | 49.46 | 1.65 |
| 2321 | >25 | 48.20 | 1.65 |
| 2320 | >25 | 52.74 | 1.62 |
| 2158 | >25 | 49.17 | 1.61 |
| 1277 | >25 | 49.76 | 1.59 |
| 2049 | >25 | 48.45 | 1.58 |
| 1387 | >25 | 47.01 | 1.57 |
| 1276 | >25 | 56.20 | 1.56 |
| 2103 | >25 | 58.83 | 1.54 |
| 1661 | >25 | 47.95 | 1.53 |
| 2211 | >25 | 47.22 | 1.47 |
| 1665 | >25 | 46.98 | 1.47 |
| 2226 | >25 | 48.85 | 1.45 |
| 2137 | >25 | 47.90 | 1.44 |
| 2210 | >25 | 68.51 | 1.41 |
| 2239 | >25 | 68.52 | 1.39 |
| 882 | >25 | 72.05 | 1.39 |
| 2079 | >25 | 50.47 | 1.39 |
| 2017 | >25 | 47.38 | 1.35 |
| 2337 | >25 | 46.66 | 1.33 |
| 2275 | >25 | 46.09 | 1.32 |
| 2348 | >25 | 72.41 | 1.26 |
| 2069 | >25 | 80.30 | 1.19 |
| 2391 | >25 | 82.32 | 1.16 |
| 2327 | >25 | 84.60 | 1.14 |
| 1324 | >25 | 89.11 | 1.12 |
| 1978 | >25 | 86.78 | 1.11 |
| 2198 | >25 | 46.75 | 1.08 |
| 2338 | >25 | 44.73 | 1.08 |
| 2123 | >25 | 93.46 | 1.07 |
| 1956 | >25 | 93.63 | 1.07 |
| 1662 | >25 | 95.00 | 1.05 |
| 2165 | >25 | 94.07 | 1.05 |
| 1664 | >25 | 88.13 | 1.04 |

Example 4

Lead Efflux Inhibitor Screening

To explore suitability of polyamine derivatives as EPIs, a library of 188 individual compounds contained within the Torrey Pines chemical collection were screened for their ability to decrease the 50% and 90% effective concentration of tetracycline towards *P. aeruginosa* (TABLE 4). However, these studies were expanded to include $EC_{50}$ determinations as well as $EC_{90}$ to provide depth to our structure activity relationship analysis.

TABLE 4

Potentiation assessment of a polyamine-derived library of compounds. All data pertains to either 50% effective concentrations ($EC_{50}$)*, or 90% effective concentrations ($EC_{90}$)#, which are defined as a 50% or 90% decrease, respectively, in the optical density values for cultures when read at 600 nm, compared to untreated controls. TPI columns refer to the inhibitory concentration of the polyamines alone (μg ml−1) to produce EC values (note that 25 μg mL−1 was the highest concentration tested in these assays). TET + TPI display the tetracycline concentration required to produce EC values (μM) in the presence of 25 μg mL−1 of the respective TPI. Fold Potentiation (FP) = EC tetracycline concentration with no TPI/EC tetracycline concentration with TPI. All assays were performed in triplicate alongside no drug controls, tetracycline alone controls (data not shown due to repetitive values, average concentration for $EC_{50}$ across all replicates = 47.75 μM; $EC_{90}$ = 82.5 μM) and the original 2229 TPL. TPI polyamines chosen as lead agents are underlined. The table list polyamines that do not have antibacterial activity alone above the compounds that have inhibitory concentrations themselves. Following this segregation, the compounds were ordered by fold potentiation of 90% effective concentration (FP#).

| TPI | TPI | FP* | TET + TPI* | FP# | TET + TPI# |
|---|---|---|---|---|---|
| 414 | >25 | 18.2 | 4 | 16.4 | 6 |
| 271 | >25 | 8.2 | 5 | 8.5 | 10 |
| 393 | >25 | 6.4 | 9 | 8 | 12 |
| 338 | >25 | 10.7 | 5 | 7.9 | 12 |
| 250 | >25 | 7 | 9 | 7.8 | 12 |
| 247 | >25 | 5 | 9 | 7.5 | 12 |
| 314 | >25 | 5 | 9 | 7.5 | 12 |
| 266 | >25 | 6.8 | 9 | 5.8 | 16 |
| 453 | >25 | 7 | 6 | 5.7 | 15 |
| 348 | >25 | 8.9 | 9 | 5.4 | 19 |
| 334 | >25 | 4.9 | 10 | 5.1 | 18 |
| 312 | >25 | 7.8 | 9 | 4.8 | 20 |
| 370 | >25 | 4.6 | 10 | 4.3 | 22 |
| 465 | >25 | 7.4 | 10 | 4.3 | 23 |
| 299 | >25 | 3.1 | 15 | 4.2 | 24 |
| 333 | >25 | 6.9 | 10 | 4.2 | 24 |
| 388 | >25 | 4.4 | 17 | 4.2 | 24 |
| 435 | >25 | 4.7 | 16 | 4.2 | 23 |
| 306 | >25 | 6 | 11 | 4.1 | 23 |
| 331 | >25 | 6.4 | 11 | 4.1 | 24 |
| 346 | >25 | 5.5 | 11 | 4.1 | 23 |
| 289 | >25 | 4.4 | 18 | 4 | 25 |
| 326 | >25 | 4.3 | 11 | 4 | 23 |
| 288 | >25 | 4.1 | 17 | 3.9 | 24 |
| 297 | >25 | 3.6 | 19 | 3.9 | 25 |
| 290 | >25 | 2.9 | 18 | 3.7 | 25 |
| 296 | >25 | 4.2 | 11 | 3.7 | 24 |
| 408 | >25 | 5.2 | 19 | 3.6 | 27 |
| 350 | >25 | 3.3 | 17 | 3.4 | 27 |
| 351 | >25 | 120.9 | 0 | 3.3 | 24 |
| 362 | >25 | 3.4 | 14 | 3.3 | 28 |
| 295 | >25 | 2.6 | 18 | 3.1 | 29 |
| 372 | >25 | 1 | 5 | 3 | 33 |
| 291 | >25 | 7.1 | 9 | 2.9 | 34 |
| 284 | >25 | 6.1 | 9 | 2.8 | 35 |
| 369 | >25 | 2.5 | 20 | 2.4 | 39 |
| 449 | >25 | 3.6 | 21 | 2.4 | 41 |
| 300 | >25 | 4.8 | 9 | 2.3 | 39 |
| 347 | >25 | 3.5 | 22 | 2.3 | 44 |
| 374 | >25 | 2.6 | 20 | 2.3 | 39 |
| 451 | >25 | 4.9 | 17 | 2.3 | 43 |
| 353 | >25 | 2.8 | 22 | 2.2 | 43 |
| 357 | >25 | 2.3 | 20 | 2.2 | 43 |
| 358 | >25 | 2.4 | 21 | 2.2 | 42 |
| 396 | >25 | 2.8 | 26 | 2.2 | 45 |
| 427 | >25 | 3.5 | 21 | 2.2 | 43 |
| 461 | >25 | 2.6 | 20 | 2.2 | 42 |
| 253 | >25 | 7.5 | 5 | 2.1 | 45 |
| 292 | >25 | 3.8 | 20 | 2.1 | 47 |
| 395 | >25 | 2.2 | 35 | 2.1 | 48 |
| 399 | >25 | 2.7 | 37 | 2.1 | 48 |
| 424 | >25 | 2.7 | 37 | 2.1 | 48 |

TABLE 4-continued

Potentiation assessment of a polyamine-derived library of compounds. All data pertains to either 50% effective concentrations (EC$_{50}$)*, or 90% effective concentrations (EC$_{90}$)#, which are defined as a 50% or 90% decrease, respectively, in the optical density values for cultures when read at 600 nm, compared to untreated controls. TPI columns refer to the inhibitory concentration of the polyamines alone (μg ml$^{-1}$) to produce EC values (note that 25 μg mL$^{-1}$ was the highest concentration tested in these assays). TET + TPI display the tetracycline concentration required to produce EC values (μM) in the presence of 25 μg mL$^{-1}$ of the respective TPI. Fold Potentiation (FP) = EC tetracycline concentration with no TPI/EC tetracycline concentration with TPI. All assays were performed in triplicate alongside no drug controls, tetracycline alone controls (data not shown due to repetitive values, average concentration for EC$_{50}$ across all replicates = 47.75 μM; EC$_{90}$ = 82.5 μM) and the original 2229 TPL. TPI polyamines chosen as lead agents are underlined. The table list polyamines that do not have antibacterial activity alone above the compounds that have inhibitory concentrations themselves. Following this segregation, the compounds were ordered by fold potentiation of 90% effective concentration (FP#).

| TPI | TPI | FP* | TET + TPI* | FP# | TET + TPI# |
|---|---|---|---|---|---|
| 432 | >25 | 2.8 | 36 | 2.1 | 48 |
| 446 | >25 | 3.1 | 22 | 2.1 | 46 |
| 447 | >25 | 2.8 | 35 | 2.1 | 48 |
| 294 | >25 | 3.2 | 17 | 2 | 47 |
| 298 | >25 | 1.9 | 24 | 2 | 45 |
| 305 | >25 | 2 | 35 | 2 | 48 |
| 313 | >25 | 2.2 | 34 | 2 | 49 |
| 319 | >25 | 2.1 | 34 | 2 | 48 |
| 354 | >25 | 2.3 | 28 | 2 | 47 |
| 361 | >25 | 2.1 | 24 | 2 | 46 |
| 365 | >25 | 2.5 | 22 | 2 | 45 |
| 373 | >25 | 2.1 | 23 | 2 | 44 |
| 380 | >25 | 2.1 | 35 | 2 | 48 |
| 382 | >25 | 2.2 | 21 | 2 | 46 |
| 386 | >25 | 1.9 | 29 | 2 | 47 |
| 409 | >25 | 2 | 37 | 2 | 49 |
| 417 | >25 | 1 | 6 | 2 | 50 |
| 420 | >25 | 2 | 38 | 2 | 49 |
| 423 | >25 | 2.7 | 37 | 2 | 49 |
| 433 | >25 | 2 | 37 | 2 | 50 |
| 437 | >25 | 2.1 | 23 | 2 | 46 |
| 441 | >25 | 1.9 | 38 | 2 | 49 |
| 303 | >25 | 1.8 | 30 | 1.9 | 47 |
| 304 | >25 | 1.8 | 33 | 1.9 | 49 |
| 327 | >25 | 1.8 | 36 | 1.9 | 48 |
| 335 | >25 | 1.4 | 36 | 1.9 | 47 |
| 378 | >25 | 1.7 | 30 | 1.9 | 49 |
| 383 | >25 | 1.9 | 22 | 1.9 | 44 |
| 389 | >25 | 1.4 | 37 | 1.9 | 49 |
| 397 | >25 | 1.8 | 28 | 1.9 | 49 |
| 436 | >25 | 1.9 | 38 | 1.9 | 52 |
| 442 | >25 | 2.1 | 39 | 1.9 | 52 |
| 252 | >25 | 5.8 | 10 | 1.8 | 50 |
| 285 | >25 | 6.9 | 5 | 1.8 | 52 |
| 309 | >25 | 1.1 | 33 | 1.8 | 49 |
| 310 | >25 | 1.6 | 26 | 1.8 | 49 |
| 311 | >25 | 1.3 | 31 | 1.8 | 46 |
| 317 | >25 | 5.6 | 8 | 1.8 | 55 |
| 429 | >25 | 1.6 | 35 | 1.8 | 49 |
| 301 | >25 | 1.2 | 31 | 1.7 | 50 |
| 343 | >25 | 1.1 | 34 | 1.7 | 47 |
| 445 | >25 | 1.3 | 32 | 1.7 | 49 |
| 463 | >25 | 2.7 | 38 | 1.7 | 59 |
| 293 | >25 | 5 | 9 | 1.6 | 61 |
| 307 | >25 | 1.3 | 28 | 1.5 | 48 |
| 316 | >25 | 1.7 | 32 | 1.5 | 66 |
| 342 | >25 | 1.3 | 37 | 1.5 | 60 |
| 377 | >25 | 1.4 | 38 | 1.5 | 63 |
| 375 | >25 | 1.5 | 24 | 1.4 | 45 |
| 425 | >25 | 1.9 | 39 | 1.4 | 72 |
| 321 | >25 | 1.8 | 39 | 1.3 | 75 |
| 330 | >25 | 1.7 | 37 | 1.3 | 74 |
| 345 | >25 | 1.8 | 34 | 1.3 | 72 |
| 387 | >25 | 2.1 | 37 | 1.3 | 77 |
| 457 | >25 | 1.8 | 41 | 1.3 | 78 |
| 464 | >25 | 2.4 | 41 | 1.3 | 77 |
| 318 | >25 | 1.2 | 32 | 1.2 | 62 |
| 329 | >25 | 1.7 | 43 | 1.2 | 83 |
| 341 | >25 | 1.8 | 42 | 1.2 | 80 |
| 355 | >25 | 1.7 | 44 | 1.2 | 86 |
| 401 | >25 | 1.6 | 42 | 1.2 | 85 |
| 418 | >25 | 2.4 | 42 | 1.2 | 86 |
| 438 | >25 | 1.6 | 42 | 1.2 | 80 |
| 450 | >25 | 1.9 | 44 | 1.2 | 85 |
| 458 | >25 | 1.9 | 42 | 1.2 | 83 |
| 308 | >25 | 4 | 16 | 1.1 | 87 |
| 323 | >25 | 1.1 | 67 | 1.1 | 93 |
| 324 | >25 | 1.1 | 67 | 1.1 | 93 |
| 325 | >25 | 1.3 | 55 | 1.1 | 91 |
| 332 | >25 | 1 | 23 | 1.1 | 93 |
| 336 | >25 | 1.8 | 21 | 1.1 | 44 |
| 337 | >25 | 1.6 | 45 | 1.1 | 88 |
| 339 | >25 | 1.1 | 73 | 1.1 | 95 |
| 340 | >25 | 1.2 | 65 | 1.1 | 93 |
| 356 | >25 | 1.1 | 65 | 1.1 | 93 |
| 363 | >25 | 1.4 | 59 | 1.1 | 92 |
| 364 | >25 | 1.2 | 63 | 1.1 | 93 |
| 371 | >25 | 1.6 | 48 | 1.1 | 89 |
| 379 | >25 | 1.4 | 55 | 1.1 | 91 |
| 381 | >25 | 1.5 | 33 | 1.1 | 81 |
| 400 | >25 | 2.2 | 46 | 1.1 | 89 |
| 402 | >25 | 2 | 49 | 1.1 | 90 |
| 411 | >25 | 1.7 | 45 | 1.1 | 87 |
| 412 | >25 | 1.6 | 48 | 1.1 | 89 |
| 416 | >25 | 1.4 | 71 | 1.1 | 94 |
| 426 | >25 | 1.5 | 66 | 1.1 | 94 |
| 428 | >25 | 1.3 | 56 | 1.1 | 91 |
| 431 | >25 | 2.1 | 49 | 1.1 | 89 |
| 434 | >25 | 1.4 | 66 | 1.1 | 94 |
| 439 | >25 | 1.6 | 63 | 1.1 | 93 |
| 440 | >25 | 1.8 | 55 | 1.1 | 91 |
| 443 | >25 | 1.2 | 67 | 1.1 | 94 |
| 444 | >25 | 1.8 | 45 | 1.1 | 87 |
| 448 | >25 | 1.9 | 51 | 1.1 | 90 |
| 455 | >25 | 1.5 | 65 | 1.1 | 93 |
| 456 | >25 | 1.5 | 66 | 1.1 | 93 |
| 459 | >25 | 1.2 | 67 | 1.1 | 93 |
| 315 | >25 | 6.7 | 6 | 1 | 74 |
| 419 | >25 | 1.2 | 65 | 1 | 93 |
| 403 | 18 | 113.3 | 1 | 120.9 | 1 |
| 407 | 17 | 80.8 | 1 | 62.9 | 2 |
| 391 | 9 | 27.3 | 1 | 20.3 | 2 |
| 385 | 16 | 17.9 | 3 | 17.5 | 5 |
| 376 | 4 | 142.1 | 0 | 11.9 | 4 |
| 430 | 15 | 13.8 | 5 | 10.5 | 9 |
| 384 | 4 | 142.5 | 0 | 10.3 | 5 |
| 287 | 22 | 8.6 | 5 | 9 | 9 |
| 460 | 14 | 11.1 | 7 | 8.4 | 12 |
| 422 | 14 | 9 | 8 | 8.3 | 11 |
| 404 | 11 | 8.3 | 9 | 8.3 | 11 |
| 421 | 15 | 8.8 | 6 | 8 | 11 |
| 454 | 14 | 9.5 | 6 | 8 | 12 |
| 462 | 14 | 9.5 | 6 | 8 | 12 |
| 390 | 22 | 5.1 | 9 | 7.5 | 12 |

TABLE 4-continued

Potentiation assessment of a polyamine-derived library of compounds. All data pertains to either 50% effective concentrations (EC$_{50}$)*, or 90% effective concentrations (EC$_{90}$)#, which are defined as a 50% or 90% decrease, respectively, in the optical density values for cultures when read at 600 nm, compared to untreated controls. TPI columns refer to the inhibitory concentration of the polyamines alone (μg ml$^{-1}$) to produce EC values (note that 25 μg mL$^{-1}$ was the highest concentration tested in these assays). TET + TPI display the tetracycline concentration required to produce EC values (μM) in the presence of 25 μg mL$^{-1}$ of the respective TPI. Fold Potentiation (FP) = EC tetracycline concentration with no TPI/EC tetracycline concentration with TPI. All assays were performed in triplicate alongside no drug controls, tetracycline alone controls (data not shown due to repetitive values, average concentration for EC$_{50}$ across all replicates = 47.75 μM; EC$_{90}$ = 82.5 μM) and the original 2229 TPL. TPI polyamines chosen as lead agents are underlined. The table list polyamines that do not have antibacterial activity alone above the compounds that have inhibitory concentrations themselves. Following this segregation, the compounds were ordered by fold potentiation of 90% effective concentration (FP#).

| TPI | TPI | FP* | TET + TPI* | FP# | TET + TPI# |
|---|---|---|---|---|---|
| 286 | 22 | 8.5 | 7 | 5.9 | 17 |
| 452 | 18 | 7.7 | 10 | 4.9 | 21 |
| 272 | 24 | 7.7 | 9 | 4.6 | 20 |
| 410 | 18 | 9.9 | 10 | 4.5 | 22 |
| 394 | 25 | 4.9 | 10 | 4.1 | 22 |
| 415 | 21 | 5.3 | 19 | 4.1 | 25 |
| 349 | 14 | 6.7 | 9 | 4.1 | 23 |
| 398 | 11 | 4.2 | 11 | 4.1 | 21 |
| 328 | 1 | 4.8 | 8 | 4.1 | 12 |
| 366 | 19 | 2.5 | 19 | 3.7 | 25 |
| 405 | 25 | 7.2 | 10 | 3.4 | 27 |
| 359 | 25 | 2 | 19 | 2.8 | 24 |
| 406 | 18 | 3.8 | 20 | 2.6 | 36 |
| 392 | 15 | 3.3 | 10 | 2.4 | 20 |
| 367 | 2 | 1.7 | 19 | 2.3 | 32 |
| 413 | 19 | 3.6 | 19 | 2 | 47 |
| 368 | 6 | 3 | 11 | 1.9 | 25 |
| 352 | 3 | 2.3 | 15 | 1.8 | 27 |
| 269 | 23 | 9.7 | 5 | 1.5 | 66 |
| 360 | 9 | 1.7 | 20 | 1.3 | 38 |
| 320 | 24 | 1.9 | 20 | 1.2 | 42 |
| 344 | 10 | 1.5 | 23 | 1.1 | 46 |

Figure 2:
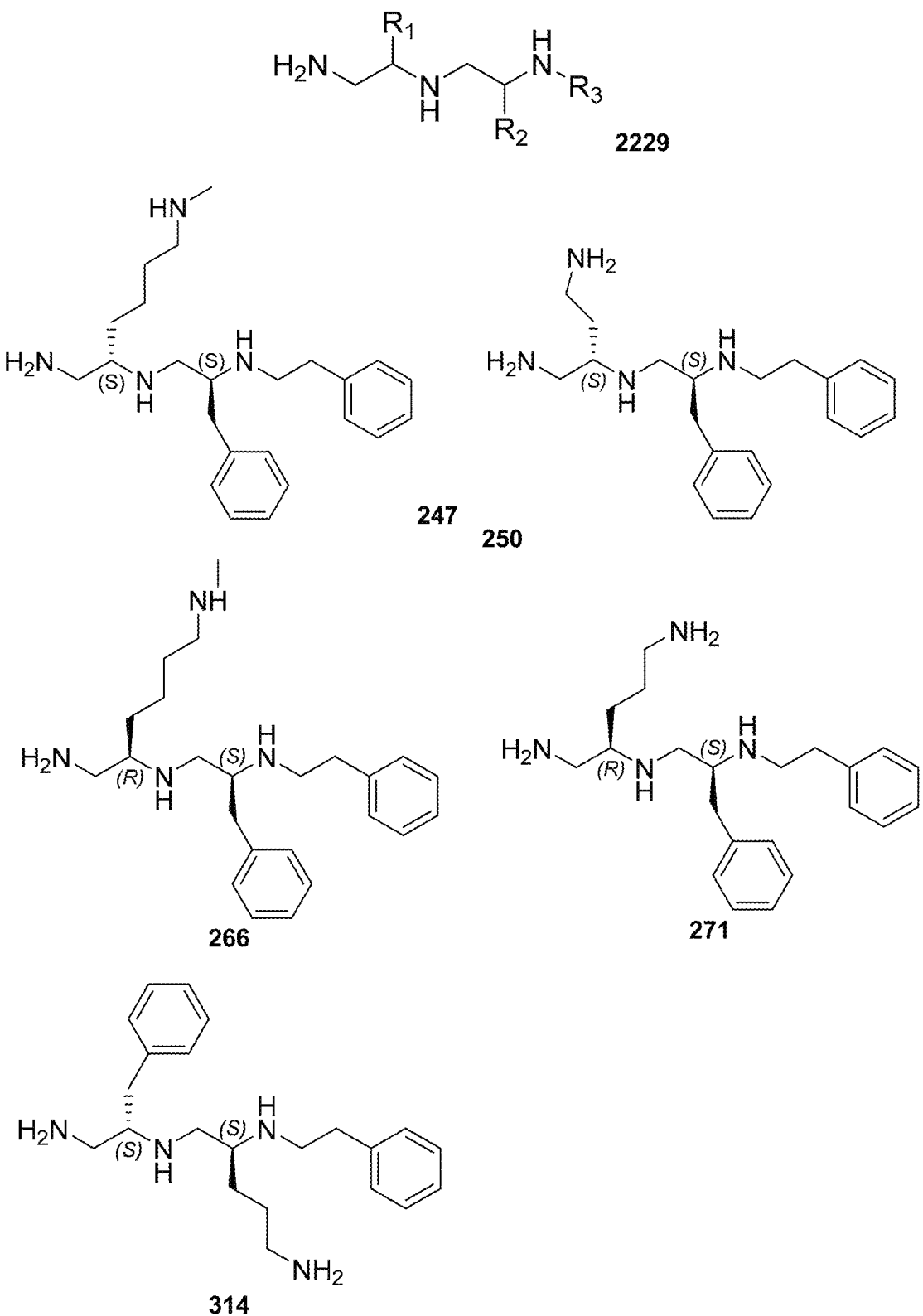
FIG. 2 shows the structure of the core polyamine scaffold (2229) and individual polyamine lead molecules 247, 250, 266, 271, and 314.

Upon analysis, 37 individual polyamines were found to inhibit bacterial growth alone at or below the maximum concentration tested 25 μg mL$^{-1}$. Of the 151 remaining polyamines, 72 reduced the tetracycline EC$_{50}$ by <2-fold, 30 decreased the tetracycline EC$_{50}$ between 2-5-fold, and 49 decreased the tetracycline EC$_{50}$ by 5-fold. From this latter group, 10 were also successful at decreasing the 90% effective concentration by 5-fold. Four of the 10 most effective polyamines (247, 250, 266, 271) had an amine functionality at the R1 position, S-methylbenezene at the R2 position, and ethylbenzene at the R3 position. Interestingly, both stereoisomers of methylbutylamine (247=S—N-methylbutylamine; 266=R—N-methylbutylamine) were found to create strong potentiation at the R1 position. From the remaining six polyamines, three (314, 338, and 348) had S-methylbenezene at the R1 position, an amine functionality at the R2 position, and ethylbenzene at the R3 position; while three (393, 414, and 453) had S-methylbenezene at the R1 and R2, and varied aromatic groups at the R3 position; thus, lacking an amine functionality at the R1 or R2 position. Although polyamines 393, 414, and 453 displayed promising fold-potentiation values, these agents were not selected as lead agents when considering that a large portion (24%) of polyamines with the R1 and R2 functionality defined by S-methylbenezene displayed antibacterial activity themselves. In contrast however, the majority (52%) of polyamines with S-methylbenezene at the R2 and R3 positions displayed 2-fold potentiation of tetracycline activity without displaying inhibition alone. Therefore, we prioritized polyamines with amine functionalities at the R1 position (247, 250, 266, 271), as this was the most promising orientation for the positive charge. In addition, while the 10 most potentiating polyamines were shown to decrease the EC$_{50}$ of tetracycline from 47.8 μM to 9 μM, there were a subset of four agents (247, 250, 271, 314) that were more effective at decreasing the EC$_{90}$ than the EC$_{50}$ revealing their activity does not plateau before 90% bacterial inhibition is achieved. Therefore, we chose polyamines 247, 250, 266, 271, 314 from the 10 most potentiating polyamines to undergo secondary validation assessment to explore their EPI-like properties (FIG. 2).

Figure 3A:
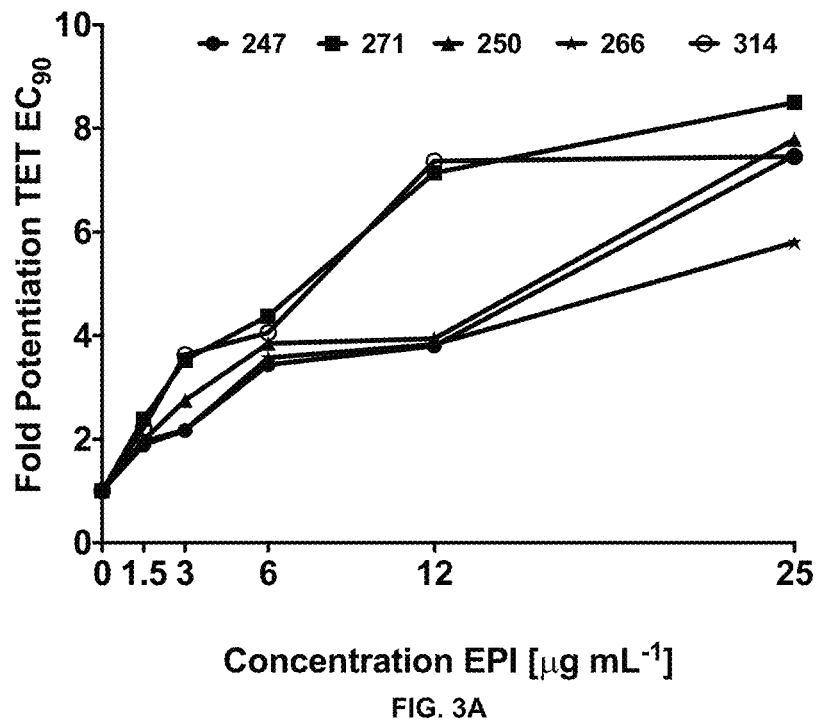
FIG. 3A and FIG. 3B are graphs showing that the polyamine lead agents potentiate the activity of unrelated antibiotic efflux substrates. *P. aeruginosa* cells were treated with polyamine molecules at increasing concentrations, alongside tetracycline (FIG. 3A) or chloramphenicol (FIG. 3B). Shown is the fold potentiation of each antibiotic ($EC_{90}$ values) as the EPI concentration was increased.
Figure 10A:
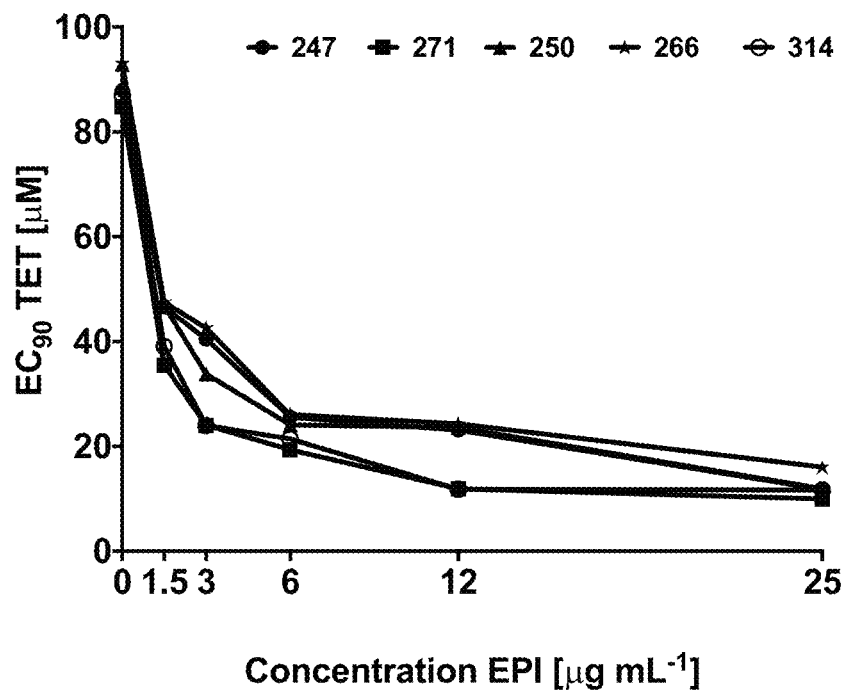
FIG. 10A and FIG. 10B are graphs showing that the front runner polyamines potentiate the activity of unrelated antibiotic efflux substrates. *P. aeruginosa* cells were treated with polyamine agents at increasing concentrations, alongside tetracycline (FIG. 10A) or chloramphenicol (FIG. 10B). Shown is the potentiated EC$_{90}$ concentrations for each antibiotic at increasing EPI concentrations.

Using dose response studies (FIG. 3A, FIG. 10A, and FIG. 9), we determined that the most effective lead was compound 271, potentiating the tetracycline EC$_{90}$ by 8.5-fold and its EC$_{50}$ by 8.2-fold (TABLE 1). With regards to the remaining four compounds, we determined that 247 resulted in an 8.3-fold decrease of the EC$_{90}$ and a 5-fold decrease of the EC$_{50}$. Of note, these two compounds are similar with S-methylbenezene at the R2 position, and ethylbenzene at the R3 position, however, they differ slightly at the R1 position (247=S—N-methylbutylamine; 271=R—N-propylamine). Additionally, compounds 250 and 266 both display a 7.8-fold and 5.8-fold potentiation of the tetracycline EC$_{90}$ respectively, with strong EC$_{50}$ values of 7.0 and 6.8-fold potentiation. Interestingly, 266 displayed more promising EC$_{50}$ fold-potentiation than EC$_{90}$, however this is a common feature of competitive EPIs (Askoura, et al. Libyan Journal of Medicine 2011, 6); indeed, our studies reveal a similar effect for the well described EPIs reserpine and PAN (TABLE 1). Both 250 and 266 also have S-methylbenezene at the R2 position and ethylbenzene at the R3 position similar to compounds 247 and 271, but again vary at the R1 position (250=S-ethylamine; 266=R—N-methylbutylamine). Compound 314 was found to have EC$_{50}$ and EC$_{90}$, fold potentiation values of 5 and 7.5-fold, respectively. Of note, 314 has an S-methylbenzene at the R1 position and an amine functionality (this time propylamine) at the R2.

TABLE 1

Potentiation assessment of lead polyamine compounds.

| | EPI*$^a$ | TET + EPI*$^b$ | FP*$^c$ | TET + EPI#$^b$ | FP#$^c$ |
|---|---|---|---|---|---|
| 247 | >25 | 9 | 5.0 | 12 | 8.3 |
| 250 | >25 | 9 | 7.0 | 12 | 7.8 |
| 266 | >25 | 9 | 6.8 | 16 | 5.8 |
| 271 | >25 | 5 | 8.2 | 10 | 8.5 |
| 314 | >25 | 9 | 5.0 | 12 | 7.5 |
| Reserpine | >25 | 4 | 11.2 | >50 | 1 |
| PAβN | >25 | 0.7 | 65.5 | 11.63 | 8 |

*50% effective concentrations (EC$_{50}$).
90% effective concentrations (EC$_{90}$).
$^a$EPI is the inhibitory concentration of the individual Efflux Pump Inhibitor (EPI) alone (μg mL$^{-1}$).
$^b$TET + EPI is the respective EC tetracycline (μM) in the presence of each compound.
$^c$FP is Fold Potentiation = EC tetracycline + EPI/EC tetracycline (no EPI).

Figure 3B:
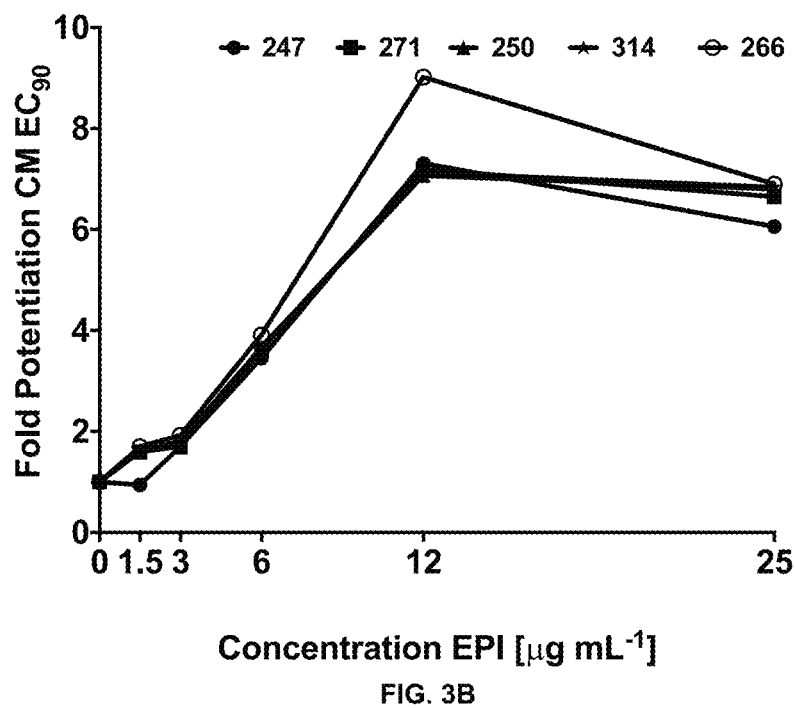
Figure 10B:
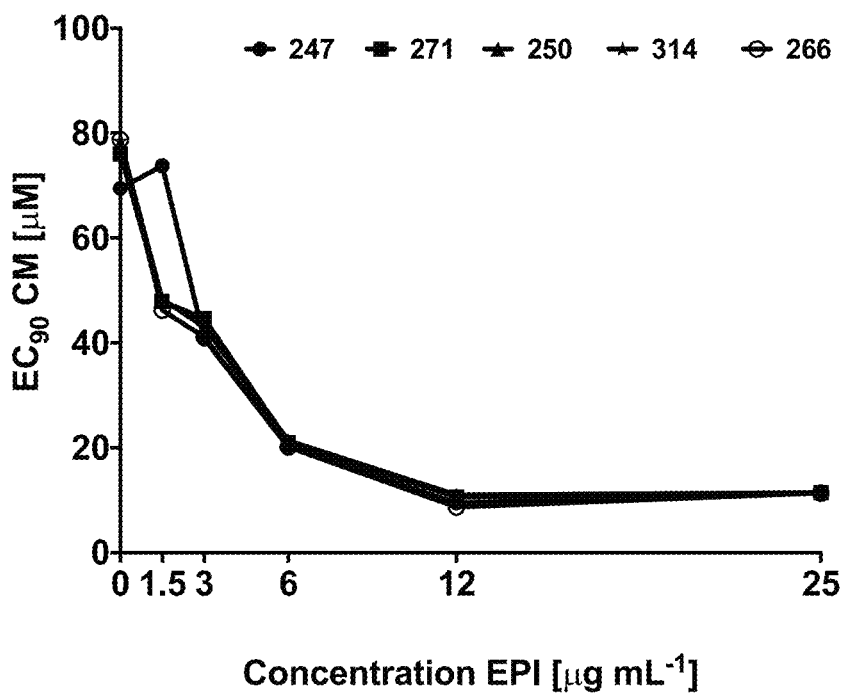

To confirm that the activity of our lead agents was not merely confined to tetracycline, we next explored the potentiation of an unrelated antibiotic efflux substrate, chloramphenicol (FIG. 3B, FIG. 10B, and FIG. 9). Each of the polyamine agents again displayed an increase in the potentiation of chloramphenicol EC$_{90}$ in a dose responsive manner. Agent 266 displayed the highest potentiation values, although all compounds performed in a markedly similar, and effective manner. As such, it would appear that our polyamines are capable of potentiating the activity of multiple antibiotic substrates in *P. aeruginosa* strains, which speaks to their utility for further development.

Example 5

Polyamines Function Via the Inhibition of Bacterial Efflux Mechanisms

Figure 4A:
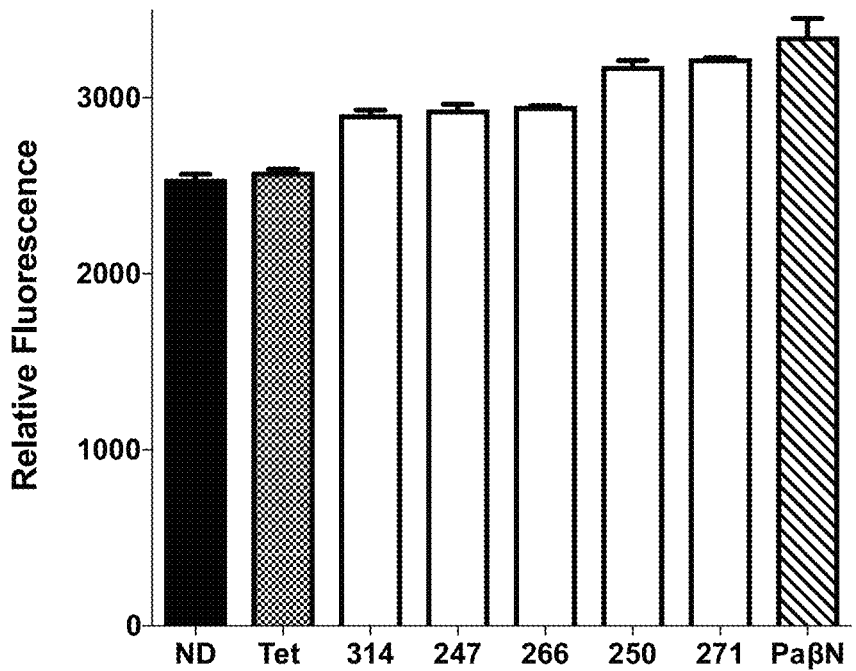
FIG. 4A and FIG. 4B are graphs showing that the polyamine molecules have broad spectrum EPI activity. *P. aeruginosa* (FIG. 4A) or *A. baumannii* (FIG. 4B) cells were treated with a sub-lethal concentration of ethidium bromide (25 µM) in combination with tetracycline, the known efflux pump inhibitor PAβN, lead polyamine agents at 25 µg mL$^{-1}$, or vehicle (10% DMF) (ND). Graphs demonstrate fluorescence after 90-minute exposure displayed as relative fluorescent units. Error bars are shown ±SEM.
Figure 4B:
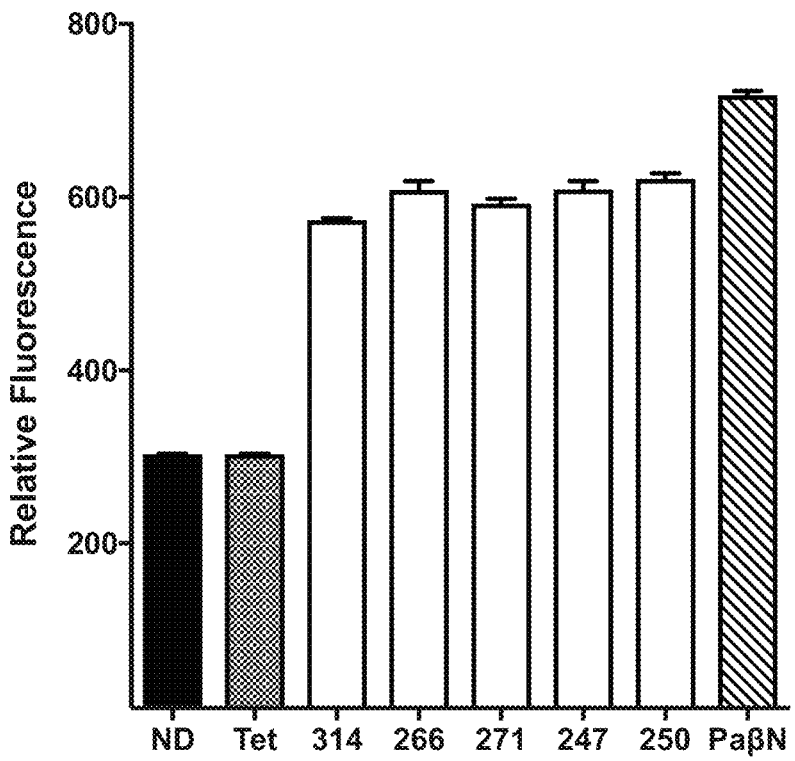
Figure 11A:
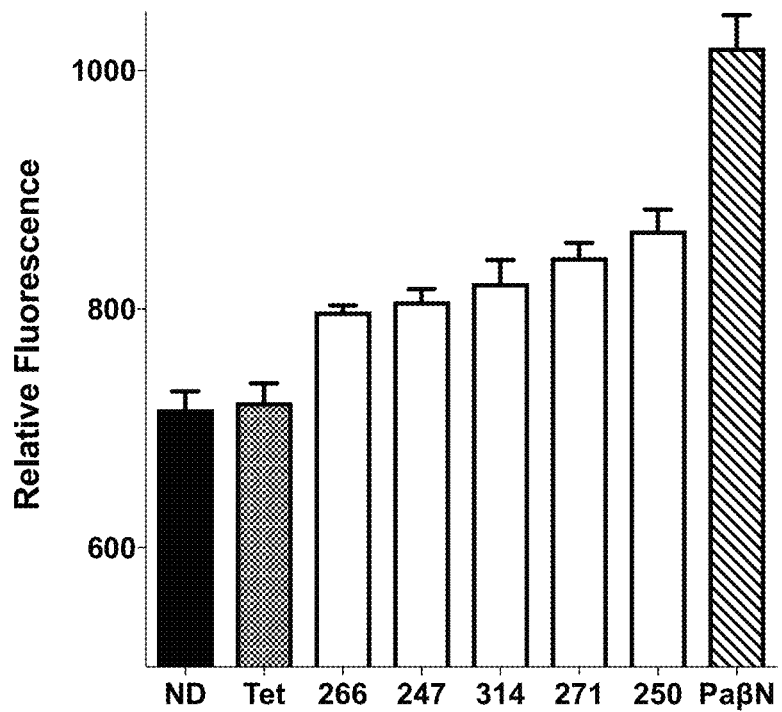
FIG. 11A and FIG. 11B are graphs showing that the polyamine molecules have broad spectrum EPI activity. *E. faecium* cells (FIG. 11A) and *S. aureus* cells (FIG. 11B) were treated with a sub-lethal concentration of ethidium bromide (25 µM) in combination with no drug controls (ND), tetracycline (negative control), the known efflux pump inhibitor PAβN, or lead polyamine agents all at 68 µM or 25 µg mL$^{-1}$. Graphs demonstrate fluorescence after 90-minute exposure displayed as relative fluorescent units. Error bars are shown ±SEM.
Figure 11B:
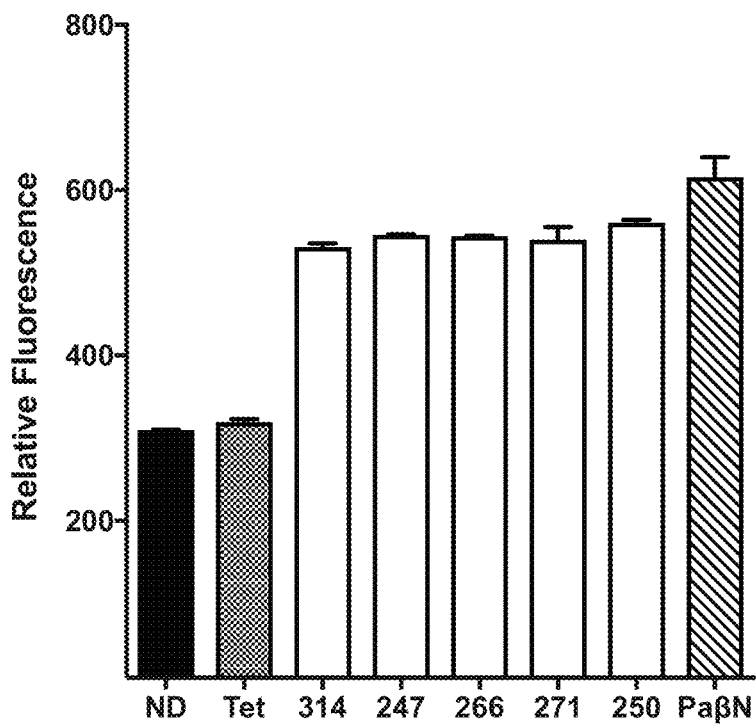

Following these promising results, we sought to validate our findings using more direct means. Accordingly, the polyamines were assessed using an ethidium bromide fluorescence assay that has been widely used to identify efflux inhibitors (Renau, et al. *J. Med. Chem.* 1999, 42, 4928-4931; Lomovskaya, et al. *Antimicrobial Agents and Chemotherapy* 2001, 45, 105-116; Webber, et al. *PLoS One* 2013, 8, e60666; Blanchard, et al. *Antimicrobial Agents and Chemotherapy* 2014, 58, 6360-6370; Vasudevan, et al. *International Journal of Pharmacy and Pharmaceutical Sciences* 2014, 6, 84-89). Fluorescence of ethidium bromide occurs during intercalation with DNA; thus, active efflux mechanisms decrease such fluorescence by extruding ethidium bromide before it can interact with its target. Thus, disruption of EP activity leads to the accumulation of intracellular ethidium bromide and a subsequent increase in fluorescence over time compared to efflux proficient cells. Importantly, when we treated *P. aeruginosa* with lead polyamines, followed by a sub-lethal concentration of ethidium bromide, we observed an increase in fluorescence (FIG. 4A) compared to no drug controls; indicating inhibition of efflux systems. To determine if these effects are solely limited to *P. aeruginosa*, we next tested other Gram-negative pathogens. When these assays were repeated with *Acinetobacter baumannii*, we observed similar results (FIG. 4B), indicating the broad-spectrum nature of these agents. Furthermore, when we assayed the Gram-positive pathogen *Staphylococcus aureus*, we again derived similar findings (FIG. 11B; see FIG. 11A for *E. faecium*). Collectively, these data suggest that our triamine molecules are not only effective inhibitors of bacterial efflux mechanisms, but that these effects appear to be broad-spectrum in range.

Example 6

Figure 12:
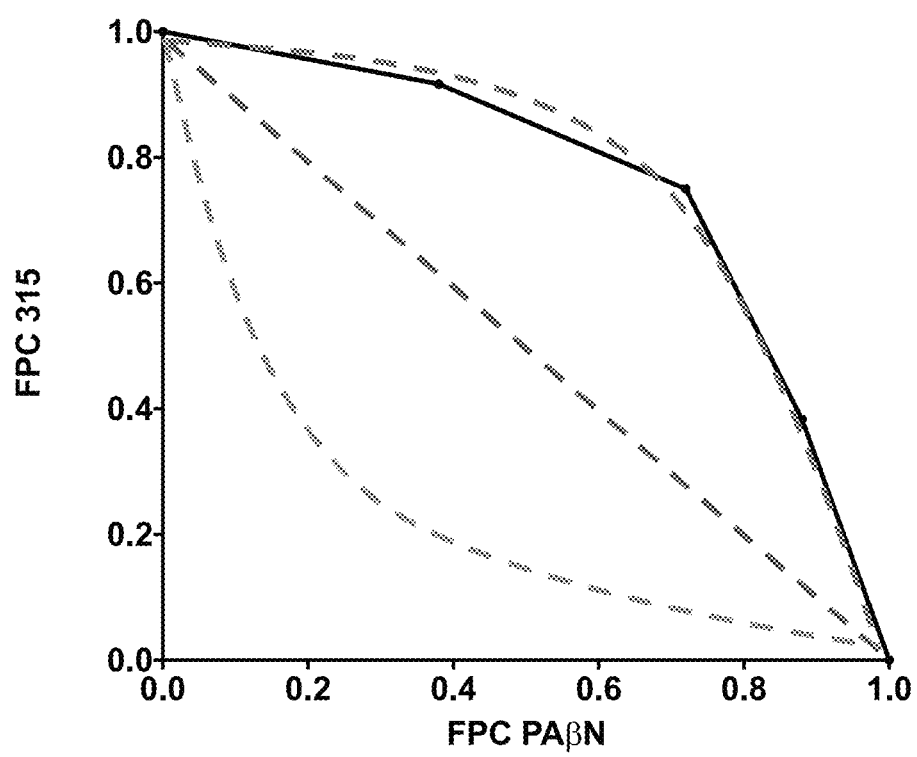
FIG. 12 is a graph showing that the polyamine molecules are antagonistic to the activity of PAβN. Depicted are hypothetical (dotted lines) and experimentally determined (solid line) representations of EPI synergy. In the experimental conditions (solid black line) *P. aeruginosa* cells were incubated with increasing concentrations of lead polyamine 315 and PAN in the presence of a fixed concentration (25 µM) of tetracycline in checkerboard assays. EC$_{90}$ values were determined and used to calculate the fractional potentiating concentration (FPC) of 315 and PAN (FPC=combination potentiating concentration/potentiating concentration alone). Shown for comparison are the hypothetical shapes of typical experimental curves, indicating synergistic (bottom dash), additive (middle dash), or antagonistic (top dash) activity for drug combinations.

Polyamines Act Competitively with PAN to Potentiate the Tetracycline Effective Concentration To further confirm the EPI activity of polyamine agents, we performed a checkerboard assessment to determine the relationship between our front runner molecules and the control compound PAβN. If our polyamine agents inhibit a target other than EPs, then combination treatment would produce a synergistic action. However, if the agents are both inhibiting EPs, the result of combination treatment would be antagonistic (Auerbach, et al. *PNAS* 2010, 107, 1983-1988; Goodman, et al. *Goodman & Gilman's pharmacological basis of therapeutics*. 2011, New York, McGraw-Hill). Upon analysis we observed a clear competitive interaction between PAN and polyamine agents in the presence of tetracycline (FIG. 12). This further confirms that the polyamine agents are inhibiting EPs of bacterial species.

Example 7

Figure 5A:
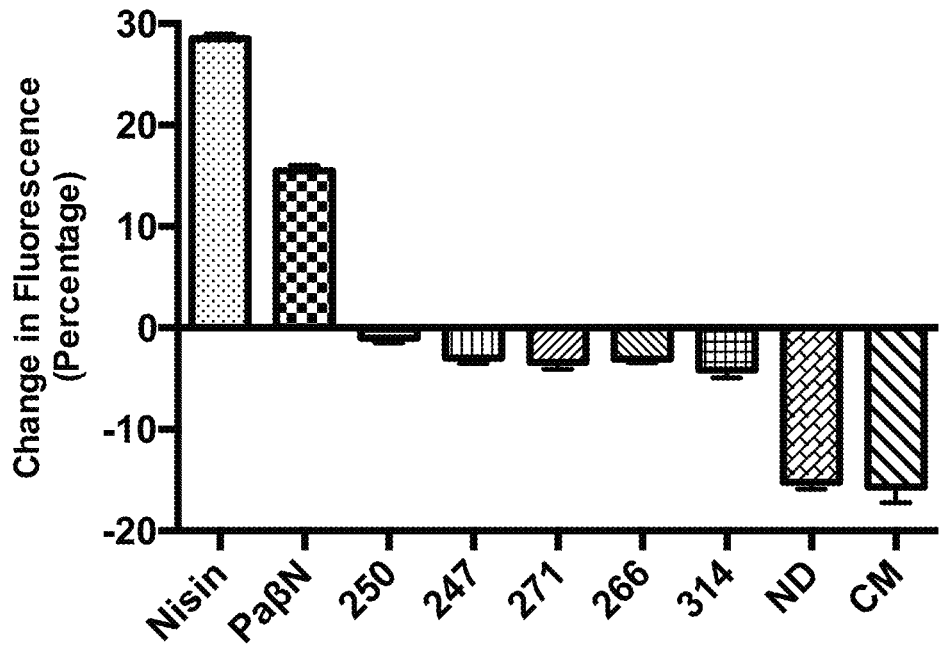
FIG. 5A and FIG. 5B are graphs showing that the polyamines do not destabilize prokaryotic or eukaryotic membranes. Shown in FIG. 5A is the change in fluorescence of *P. aeruginosa* cells using a Disc3 dye assay. Data is presented as change in fluorescence before and after addition of leads compounds, PAβN, and nisin at 25 µg mL$^{-1}$. Shown in FIG. 5B are the results of calcium channel activity assays to assess inhibition of calcium channel pumps in HEK 293 cells after the addition of polyamines 250, 266, 271 or the positive control verapamil at 25 µg mL$^{-1}$. Data is presented as change in fluorescence of cells before and after addition of the Fluo-4 dye. No drug (ND) and/or chloramphenicol (CM) were used as negative controls.

Polyamine Molecules do not Randomly Depolarize Prokaryotic or Eukaryotic Membranes A number of EPIs discovered to date have been shown to non-specifically inhibit efflux mechanisms through the non-specific depolarization of charge across bacterial membranes (Askoura, et al. *Libyan Journal of Medicine* 2011, 6; Webber, et al. *PLoS One* 2013, 8, e60666). To determine if such effects were true of our polyamines, we assessed membrane depolarization using the molecular probe $DiSC_3$. In cells with normal membrane polarity, the bacterial membrane will quench fluorescence of the $DiSC_3$ dye. However, if the membrane is depolarized, the dye is released, and fluorescence increases over time. Our results reveal that the polyamines had no effect on bacterial membranes, behaving similar to negative controls (FIG. 5A). Whilst the positive control nisin and PAN treated cell membranes displayed a strong increase in fluorescence, indicating membrane destabilization, cells treated with chloramphenicol or solvent only (10% DMF) decreased in florescence. Polyamines treated cells displayed essentially no change in fluorescence, revealing no depolarization when compared to the known efflux inhibitor PAβN.

Figure 5B:
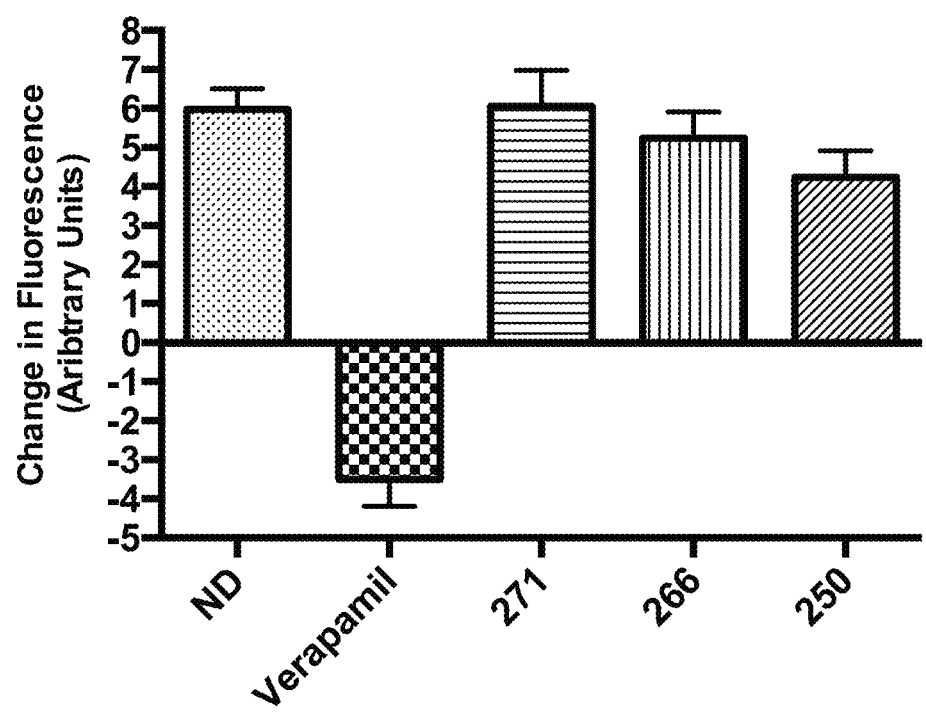

Another key consideration when developing EPIs is their impact on eukaryotic efflux systems, as many such molecules identified to date have non-specific effects on mammalian ion transport systems as well (Van Bambeke, et al. *Recent Pat. Antiinfect. Drug Discov.* 2006, 1, 157-175). As such, we tested the effects of the polyamines in this regard against human embryonic kidney epithelial cells (Hek293T), alongside the known, and toxic EPI, verapamil. In these studies, we determined that our polyamine efflux inhibitors mirrored no drug controls when assessed for their ability to interfere with eukaryotic calcium channel activity (FIG. 5B). Specifically, lead compound treated cells exhibited increased fluorescence in the presence of the Fluoro-4 dye, whilst verapamil decreased fluorescence, representing the inhibition of calcium channel activity. Thus, it would appear that our polyamines are not only specific EPIs, but that their effects are selective for prokaryotic membrane pumps, over their eukaryotic counterparts.

Example 8

Lead Polyamine EPIs Lack General Toxicity Towards Eukaryotic Cells

Given the lack of effect of polyamines towards eukaryotic ion channels, we next assessed general cytotoxicity towards human cells. As such, polyamine lead compounds were tested against both HepG2 (FIG. 6B) and Hek293T (FIG. 6A) cell lines using MTT assays). In so doing, we determined that front runners 247, 266, and 271 had extremely low toxicity towards Hek293T cells. Specifically, when treated with 25 µg $mL^{-1}$ of these compounds, cells displayed 84%, 72%, and 75% recovery compared to solvent only controls, whilst the known EPI PAN returned only 63% cell viability. In support of this, HepG2 cell recovery after treatment with 250, 314 or 271 generated similar results; even at the highest concentration tested (again 25 µg $mL^{-1}$) we observed 80%, 77%, and 74% cell viability. In comparison, the known efflux inhibitor PAN tested at the same concentration allowed for 68% recovery of HepG2 cells. The higher toxicity of PAN was perhaps unsurprising considering that this agent has been shown to depolarize membranes at higher concentrations (Webber, et al. *PLoS One* 2013, 8, e60666).

Example 9

Polyamine EPIs Strongly Enhance the Bactericidal Activity of Tetracycline

Figure 7:
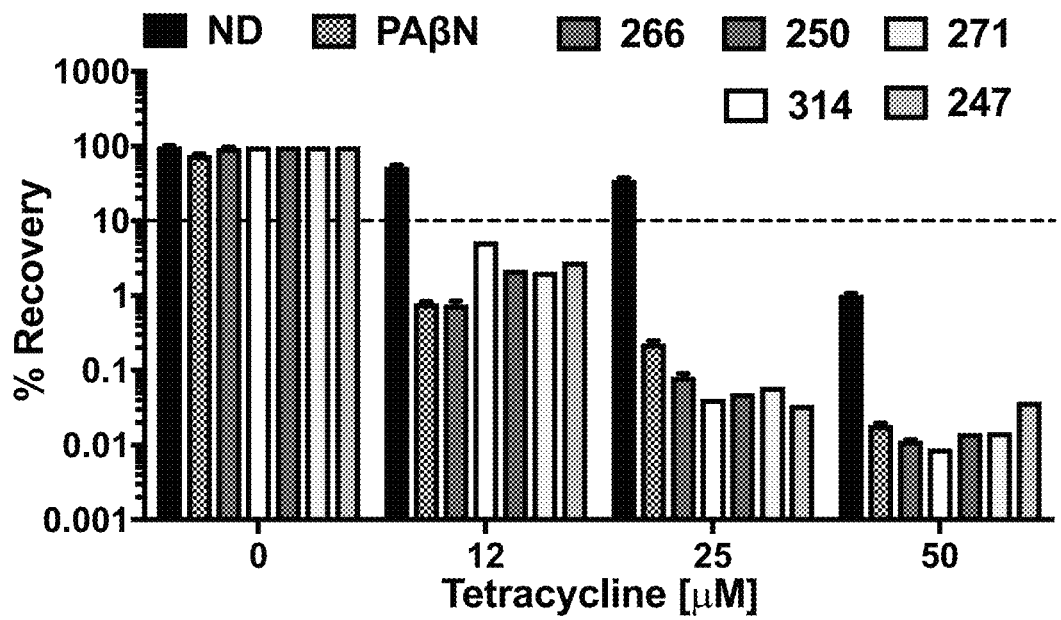
FIG. 7 is a graph showing that the polyamine EPIs strongly enhance the bactericidal activity of tetracycline. *P. aeruginosa* cells were treated with tetracycline at 0, 12, 25, and 50 µM in combination with no drug (ND), or 247, 250, 266, 271, 314 and PAN at 25 µg mL$^{-1}$. The dotted line on the graph denotes 90% bactericidal activity. Data is from at least three biological replicates, with error bars shown ±SEM.

We next set out to explore the impact of polyamines on the bactericidal effects of tetracycline. The rationale for this was that, although tetracycline is a bacteriostatic antibiotic, it is known to be bactericidal at high concentrations. Treatment with our polyamines alone at 25 µg mL$^{-1}$ resulted in minimal impact to bacterial viability, with 95% of cells recovered for all compounds, in contrast to PAN which returned only 76% viability at the same concentration. Tetracycline treatment alone at 12, 25, and 50 µM allowed for 53%, 35%, and 1% respective bacterial recovery. However, combination treatment with tetracycline and the MPC of all lead agents resulted in decreased bacterial viability. For example, combination treatment with 12 µM of tetracycline and polyamine 266 displayed the greatest decrease in bacterial viability, similar to the control PAβN. Specifically, the percent recovery decreased to 0.76% and 0.79% when treated with 266 or polyamine PaβN respectively (FIG. 7). Although not as impressive as 266 and PAβN, combination treatment with polyamines 247, 250, 271, and 314 resulted in 2.9%, 2.2%, 2%, and 5.3% recovery, respectively. Interestingly, we found that increasing tetracycline alone from 12 µM to 25 µM resulted in 17.8% less recovery, however combination treatment revealed a significant decrease in bacterial viability. In combination with 25 µM tetracycline, our polyamines appeared to outperform PAN as they allowed for 0.08% recovery, whilst combination treatment with PAN allowed for 0.2% recovery. Furthermore, 50 µM treatment with tetracycline decreased bacterial viability to 1% alone, however this was drastically decreased with combination EPI treatment. Specifically, polyamines 250, 266, and 314 resulted in the greatest decrease in bacterial recovery, allowing for 0.01% recovery. This was marginally less recovery than that of the control PAN and polyamine 271, which allowed for 0.02% recovery. Polyamine 247 displayed the least decrease in viability with combination treatment, although it still decreased bacterial recovery to 0.04%. Given that bactericidal activity is often preferred to bacteriostatic effects, particularly for immunocompromised patients, these findings are considered encouraging.

Example 10

Polyamine Potentiation of Tetracycline Activity Reduces Biofilms by *P. aeruginosa*

Figure 8:
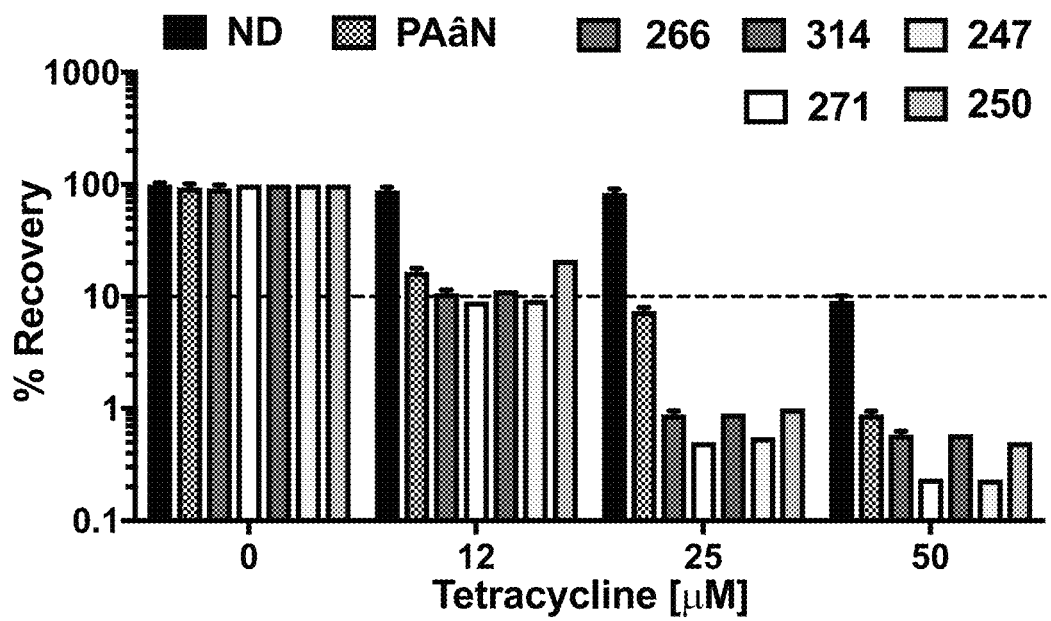
FIG. 8 is a graph showing that the polyamine potentiation of tetracycline activity limits biofilm recovery by *P. aeruginosa*. The lead polyamine agents were tested for their ability to impact viability of a pre-formed biofilm. *P. aeruginosa* cells were treated with tetracycline at 0, 12, 25, and 50 µM in combination with no drug (ND), or 247, 250, 266, 271, 314 and PAN at 25 µg mL$^{-1}$. The dotted line on the graph denotes 90% reduction in cell viability within biofilms. Data is from at least three biological replicates, with error bars shown ±SEM.

Biofilm formation is responsible for chronic, drug-resistant bacterial infections by a number of pathogens, and particularly *P. aeruginosa*. Considering the strong potentiation of tetracycline activity engendered by our lead agents, we next chose to determine if they had significant impact on the viability of cells within biofilms. Treatment with EPIs 247, 250, 266, 271, and 314 alone at 25 µg mL$^{-1}$ (maximum potentiating concentrations (MPC)) respectively, resulted in negligible impact on biofilm viability, with 99.99% of cells recovered for all compounds other than 266 which allowed for 92% recovery. Similarly, tetracycline treatment alone at 12 and 25 µM had little impact, allowing for 88% and 84% biofilm recovery, respectively (FIG. 8); only at 50 µM were more pronounced effects observed, with only 9% cells recovered. Combination treatment with 12 µM tetracycline and the MPC of all lead agents resulted in a significant decrease in biofilm recovery, however, with viability of 9.1-11% observed for 271, 247, 266, and 314 respectively. Combination treatment with lead agent 250 resulted in a slightly higher biofilm recovery of 21%, however still improving tetracycline alone biofilm eradication by 67%. Increasing tetracycline concentration by itself from 12 µM to 25 µM only resulted in 4% more eradication, however in combination with our EPIs, recovery decreased to 0.5% and 0.6% for 271 and 247 respectively. Similarly, treatment with agents 266, 250, and 314 resulted in 1% biofilm recovery. This biofilm eradication was particularly impressive when compared to the activity of the positive control PAN (7% recovery at 25 µM tetracycline). Furthermore, at the highest tetracycline concentration (50 µM) combination treatment with PaβN produced a 1% biofilm recovery while agents 271 and 247 allowed for only 0.2% recovery. Treatment with agent 250, 266, and 314 resulted in similar recovery of 0.5%, 0.6% and 0.6% respectively. These results suggest a potential benefit of combination treatment with our polyamine molecules and known efflux antibiotics to reduce biofilms.

Example 11

Discussion

The potentiating modeling utilized in this study identified polyamines that increased the effectiveness of tetracycline without displaying any toxic effects themselves. This highlights the potentiation modeling for the identification of anti-resistance agents, as opposed to synergistic agents that display antimicrobial properties as well. Potentiation modeling may be an advantageous approach to identifying adjuvant agents because synergy assessment is reliant on the therapeutic agent having antibacterial activity. Efflux pump inhibitors identified using synergistic activities, such as phenylalanine arginine beta naphthalamide (PaβN), have been unsuccessful due to off-target effects, causing bacterial growth inhibition. In contrast, concomitant treatment with an antibiotic and an efflux pump inhibitor as detailed herein that blocks the mechanism of resistance towards that antibiotic, but that has no antimicrobial properties itself, can lead to decreased resistance development. Although a subset of polyamines was discovered during our screening with antimicrobial effect themselves, their structure activity relationship was taken into consideration during lead polyamine selection as discussed in detail below, and these molecules were eliminated from further consideration.

The polyamine agents discovered in this study were successful in not only returning the effectiveness of tetracycline but also of an unrelated antibiotic efflux substrate, chloramphenicol. This finding reveals that our polyamines are not just allowing for the increased effectiveness of one, but multiple commercial antibiotics from a broad range of different classes. This finding suggests that the polyamines discovered in our study inhibit through direct competitive inhibition. This mechanism of efflux inhibition capitalizes on the broad-spectrum binding affinity of efflux pumps by blocking the substrate binding extrusion protomer on the distal binding site. Tetracycline binds to the "groove" region of the binding pocket in the binding protomer, while chloramphenicol binds to the deeper "cave" region. Covalent binding to this "cave" region is effective in efflux inhibition as it causes the binding pocket to collapse and become non-functional, therefore inhibiting multiple substrates from binding (Nikaido, et al. *FEMS Microbiol. Rev.* 2012, 36, 340-363).

The direct measurement of ethidium bromide fluorescence revealed our polyamines inhibit the efflux pumps of Gram-negative species *P. aeruginosa* and *A. baumannii*, as well as the Gram-positive organism *S. aureus*. RND is the main Gram-negative efflux system, and its absence in Gram-positive organisms reveals that if the polyamine agents are active in both Gram-positive and Gram-negative organisms, they are likely inhibiting more than one family of efflux pumps. This can be attributed to the competitive inhibition nature of efflux pump inhibitors that harnesses the broad substrate recognition of efflux pumps for more effective efflux inhibition in multiple organisms. For example, the efflux pump families of RND, ABC, SMR, and MFS all recognize substrates with polycationic properties. Further to this, RND pumps found in *P. aeruginosa* and *E. coli* recognize and extrude tetracycline, while ABC and SMR pumps in *S. aureus* also expel this same antibiotic. This may explain the activity of the previously identified efflux pump inhibitor baicalein, which is derived from the plant *Thymus vulgaris*, and has been found to potentiate tetracycline activity by blocking the MFS family TetK efflux pumps of *E. coli* and *S. aureus*. Moreover, the polyamine efflux pump inhibitors disclosed herein appear to be acting in a competitive manner with the positive control PAβN, potentially competing for the same substrate binding pocket. The polyamine efflux pump inhibitors disclosed herein resemble the known efflux pump inhibitor PAN more so than the other well-known efflux pump inhibitor 1-(1-naphthylmethyl)-piperazine (NMP), which is known not to potentiate antibiotic activity towards *P. aeruginosa*. This may explain the activity of the recent identification of a pyranopyridine inhibitor, MBX2319 that was designed based on NMP and found to have potent activity towards Enterobacteriaceae but little activity towards *P. aeruginosa*. However, a pyridopyrimidine scaffold with more similarities to PAN was found to potentiate chloramphenicol and tetracycline and further revealed to bind the distal pocket of both *P. aeruginosa* MexAB and *E. coli* AcrB, whereas MBX2319 was specific to AcrB.

We observed our polyamine efflux pump inhibitors disclosed herein did not have deleterious effects on bacterial cell membranes, as is seen for the known efflux pump inhibitor PAβN. Many efflux pump inhibitors discovered to date have been found to cause disruption of the bacterial cell membrane leading to their ineffectiveness as therapeutic agents. Disruption of the bacterial cell membrane causes inhibition of efflux through a secondary effect of membrane depolarization, leading to inhibitory activity alone, and the common identification of false positive, non-specific efflux pump inhibitors. The identification of 37 polyamines that inhibited bacterial viability themselves, lead to knowledge of a structure activity relationship for efflux pump specificity. Those polyamines found to inhibit bacterial viability themselves may be disturbing the cellular membrane based on the position of positive charges within their structure. Our analysis revealed 24% of the polyamines (26 out of 103) with $R^1$ and $R^2$ both defined by S-methylbenezene lead to antibacterial activity, while only 7% (4 out of 60) that have S-methylbenezene at $R^2$ and $R^3$, and 12% (7 out of 60) that have S-methylbenezene at $R^1$ and $R^3$, had antibacterial activity. We focused our attention on compounds that had no antibacterial activity themselves to avoid selecting membrane depolarizing agents.

We demonstrated that the efflux inhibitors detailed herein have limited toxicity towards two human cell lines and no inhibitory effects on the eukaryotic $Ca^{2+}$ channel activity of human kidney cells. To date, many efflux pump inhibitors (such as verapamil) have been shown to have non-specific inhibition of eukaryotic transporters, and therefore create unwanted side effects as therapeutic agents. Verapamil is a non-specific inhibitor of calcium channels, found to also inhibit the function of P-glycoprotein ABC transporters in mammalian cells. This inhibitor was found to have in vitro function as a bacterial efflux inhibitor, however due to its general toxicity, the use of this compound is limited to angina, hypertension, and cardiac arrhythmia. With limited toxicity and secondary effects, the polyamine efflux pump inhibitors discovered herein appear to have more favorable characteristics than others previously discovered. The polyamine efflux pump inhibitors discovered herein may have potential as adjuvant agents.

Taken together, the polyamines discovered herein may be used as therapeutic adjuvants to rescue the effects of multiple antibiotics towards both Gram-positive and Gram-negative species. They appear to be acting in a specific manner, and have none of the undesirable membrane targeting characteristics of previously developed efflux pump inhibitors. As such, we suggest that the polyamines developed herein are a promising scaffold for further development of anti-resistance agents to help alleviate the burden of multi-drug resistant bacterial pathogens.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A compound according to Formula I:

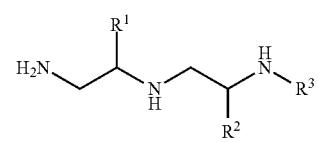

(I)

or a pharmaceutically acceptable salt thereof, wherein $R^1$ is —$(CH_2)_n$—Y;

Y is methyl, —NH—X, cycloalkyl, aryl, or heteroaryl;

X is H or methyl;

n is an integer from 0 to 10;

$R^2$ is —$(CH_2)_m$—Z;

Z is cycloalkyl, aryl, heteroaryl, or amino;

m is an integer from 0 to 5;

$R^3$ is —$(CH_2)_p$-Q;

Q is cycloalkyl, aryl, heteroaryl, or amino; and p is an integer from 0 to 5.

Clause 2. The compound of clause 1, wherein the compound is according to Formula Ia:

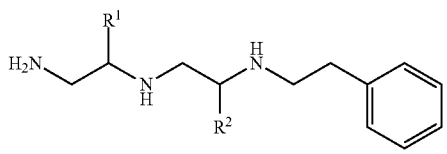

(Ia)

or a pharmaceutically acceptable salt thereof,
wherein $R^1$ is —$(CH_2)_n$—Y;
Y is methyl, —NH—X, cycloalkyl, aryl, or heteroaryl;
X is H or methyl;
n is an integer from 0 to 10;
$R^2$ is —$(CH_2)_m$—Z;
Z is cycloalkyl, aryl, heteroaryl, or amino; and
m is an integer from 0 to 5.

Clause 3. The compound of clause 1 or 2, or a pharmaceutically acceptable salt thereof, wherein Y is —NH—X, wherein X is methyl.

Clause 4. The compound of clause 1 or 2, or a pharmaceutically acceptable salt thereof, wherein Y is —NH—X, wherein X is H.

Clause 5. The compound of clause 1 or 2, or a pharmaceutically acceptable salt thereof, wherein Y is aryl.

Clause 6. The compound of clause 5, or a pharmaceutically acceptable salt thereof, wherein Y is phenyl.

Clause 7. The compound of clause 1 or 2, or a pharmaceutically acceptable salt thereof, wherein Z is aryl.

Clause 8. The compound of clause 7, or a pharmaceutically acceptable salt thereof, wherein Z is phenyl.

Clause 9. The compound of clause 1 or 2, or a pharmaceutically acceptable salt thereof, wherein Z is amino.

Clause 10. The compound of clause 1, or a pharmaceutically acceptable salt thereof, wherein Q is aryl.

Clause 11. The compound of clause 10, or a pharmaceutically acceptable salt thereof, wherein Q is phenyl.

Clause 12. The compound of any one of clauses 1-11, or a pharmaceutically acceptable salt thereof, wherein the carbon atom to which $R^1$ is attached has (S) configuration.

Clause 13. The compound of any one of clauses 1-11 or a pharmaceutically acceptable salt thereof, wherein the carbon atom to which $R^1$ is attached has (R) configuration.

Clause 14. The compound of any one of clauses 1-11, or a pharmaceutically acceptable salt thereof, wherein the carbon atom to which R2 is attached has (S) configuration.

Clause 15. The compound of any one of clauses 1-11, or a pharmaceutically acceptable salt thereof, wherein the carbon atom to which R1 is attached has (S) configuration, and the carbon atom to which R2 is attached has (S) configuration.

Clause 16. The compound of any one of clauses 1-11, or a pharmaceutically acceptable salt thereof, wherein the carbon atom to which R1 is attached has (R) configuration, and the carbon atom to which R2 is attached has (S) configuration.

Clause 17. The compound of any one of clauses 1 and 12-16, or a pharmaceutically acceptable salt thereof, wherein R1 is —(CH2)n-Y, Y is —NH—X, X is methyl, n is 4, R2 is —(CH2)m-Z wherein Z is phenyl and m is 1, and R3 is —(CH2)p-Q wherein Q is phenyl and p is 2.

Clause 18. The compound of any one of clauses 1 and 12-16, or a pharmaceutically acceptable salt thereof, wherein R1 is —(CH2)n-Y, Y is —NH—X, X is H, n is 2, R2 is —(CH2)m-Z wherein Z is phenyl and m is 1, and R3 is —(CH2)p-Q wherein Q is phenyl and p is 2.

Clause 19. The compound of any one of clauses 1 and 12-16, or a pharmaceutically acceptable salt thereof, wherein R1 is —(CH2)n-Y, Y is —NH—X, X is methyl, n is 4, R2 is —(CH2)m-Z wherein Z is phenyl and m is 1, and R3 is —(CH2)p-Q wherein Q is phenyl and p is 2.

Clause 20. The compound of any one of clauses 1 and 12-16, or a pharmaceutically acceptable salt thereof, wherein R1 is —(CH2)n-Y, Y is —NH—X, X is H, n is 3, R2 is —(CH2)m-Z wherein Z is phenyl and m is 1, and R3 is —(CH2)p-Q wherein Q is phenyl and p is 2.

Clause 21. The compound of any one of clauses 1 and 12-16, or a pharmaceutically acceptable salt thereof, wherein R1 is —(CH2)n-Y, Y is phenyl, n is 1, R2 is —(CH2)m-Z wherein Z is amino and m is 3, and R3 is —(CH2)p-Q wherein Q is phenyl and p is 2.

Clause 22. The compound of any one of clauses 2 and 12-16, or pharmaceutically acceptable salt thereof, wherein R1 is —(CH2)n-Y, Y is —NH—X, X is methyl, n is 4, and R2 is —(CH2)m-Z wherein Z is phenyl and m is 1.

Clause 23. The compound of any one of clauses 2 and 12-16, or a pharmaceutically acceptable salt thereof, wherein R1 is —(CH2)n-Y, Y is —NH—X, X is H, n is 2, and R2 is —(CH2)m-Z wherein Z is phenyl and m is 1.

Clause 24. The compound of any one of clauses 2 and 12-16, or a pharmaceutically acceptable salt thereof, wherein R1 is —(CH2)n-Y, Y is —NH—X, X is methyl, n is 4, and R2 is —(CH2)m-Z wherein Z is phenyl and m is 1.

Clause 25. The compound of any one of clauses 2 and 12-16, or a pharmaceutically acceptable salt thereof, wherein R1 is —(CH2)n-Y, Y is —NH—X, X is H, n is 3, and R2 is —(CH2)m-Z wherein Z is phenyl and m is 1.

Clause 26. The compound of any one of clauses 2 and 12-16, or a pharmaceutically acceptable salt thereof, wherein R1 is —(CH2)n-Y, Y is phenyl, n is 1, and R2 is —(CH2)m-Z wherein Z is amino and m is 3.

Clause 27. The compound of clause 1 or 2, or a pharmaceutically acceptable salt thereof, selected from the following:

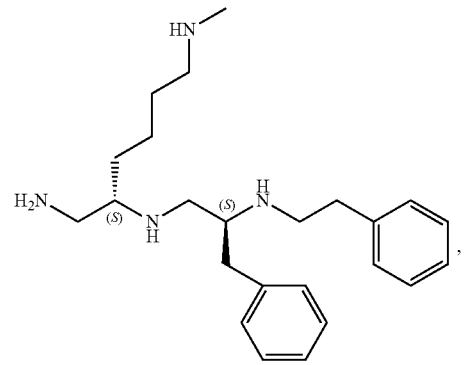

247

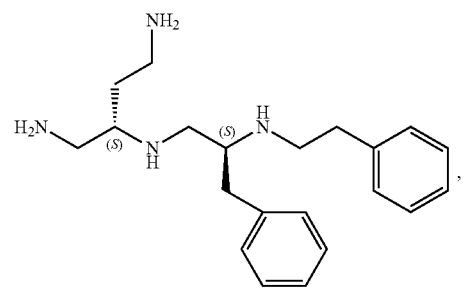

250

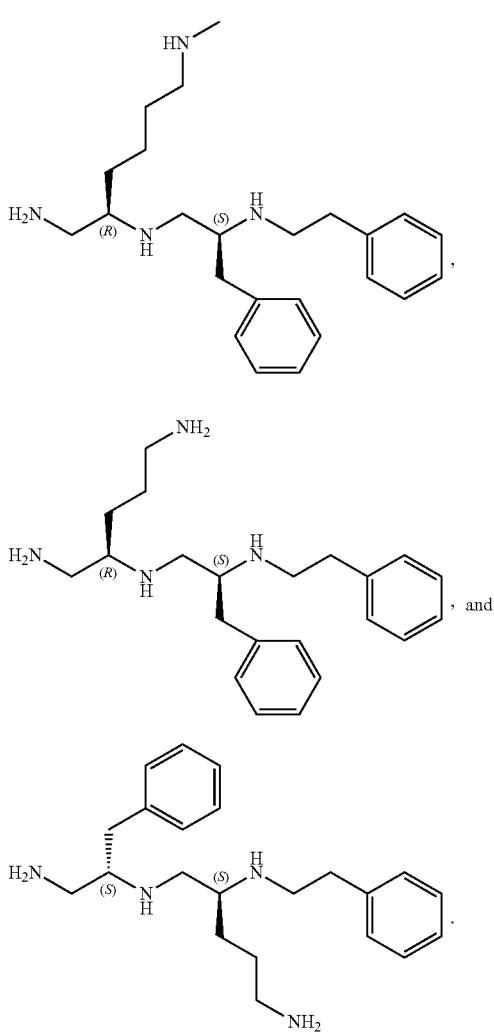

266

271

314

Clause 28. The compound of any one of clauses 1-27, or a pharmaceutically acceptable salt thereof, wherein the compound or the salt is an anti-resistance molecule.

Clause 29. The compound of any one of clauses 1-27, or a pharmaceutically acceptable salt thereof, wherein the compound or the salt is an efflux pump inhibitor.

Clause 30. The compound of clause 29, or a pharmaceutically acceptable salt thereof, wherein the compound or the salt is a bacterial efflux pump inhibitor.

Clause 31. The compound of any one of clauses 1-27, or a pharmaceutically acceptable salt thereof, wherein the compound or the salt does not disrupt bacterial membrane polarity.

Clause 32. The compound of any one of clauses 1-27, or a pharmaceutically acceptable salt thereof, wherein the compound or the salt is not toxic to a mammalian cell.

Clause 33. The compound of any one of clauses 1-27, or a pharmaceutically acceptable salt thereof, wherein the compound or the salt does not inhibit a mammalian efflux pump.

Clause 34. The compound of any one of clauses 1-27, or a pharmaceutically acceptable salt thereof, wherein the compound or the salt does not inhibit a mammalian calcium ion channel.

Clause 35. The compound of any one of clauses 1-27, or a pharmaceutically acceptable salt thereof, wherein the compound or the salt has no antibacterial activity itself.

Clause 36. The compound of any one of clauses 1-27, or a pharmaceutically acceptable salt thereof, wherein the compound or the salt reduces the therapeutic amount of an antibiotic by at least 3-fold.

Clause 37. The compound of clause 36, or a pharmaceutically acceptable salt thereof, wherein the therapeutic amount is reduced by at least 5-fold.

Clause 38. The compound of clause 36, or a pharmaceutically acceptable salt thereof, wherein the therapeutic amount is reduced by at least 8-fold.

Clause 39. The compound of any one of clauses 1-27, or a pharmaceutically acceptable salt thereof, wherein the compound or the salt reduces the minimum inhibitory concentration (MIC) of an antibiotic by at least 3-fold.

Clause 40. The compound of clause 39, or a pharmaceutically acceptable salt thereof, wherein the MIC is reduced by at least 5-fold.

Clause 41. The compound of clause 39, or a pharmaceutically acceptable salt thereof, wherein the MIC is reduced by at least 8-fold.

Clause 42. A pharmaceutical composition comprising a therapeutically effective amount of a compound of any one of clauses 1-41, or a pharmaceutically acceptable salt thereof, and a pharmaceutically acceptable carrier.

Clause 43. The pharmaceutical composition of clause 42, further comprising an antibiotic.

Clause 44. A method of preventing antibiotic resistance in a subject, the method comprising administering to the subject a therapeutically effective amount of a compound according to any one of clauses 1-41, or a pharmaceutically acceptable salt thereof, or a pharmaceutical composition of any one of clauses 42-43.

Clause 45. A method of treating a bacterial infection in a subject, the method comprising administering to the subject a therapeutically effective amount of a compound according to any one of clauses 1-41, or a pharmaceutically acceptable salt thereof, or a pharmaceutical composition of any one of clauses 42-43.

Clause 46. The method of any one of clauses 44-45, wherein the compound, or the salt, or the composition is co-administered with at least one antibiotic.

The invention claimed is:
1. A compound according to Formula I:

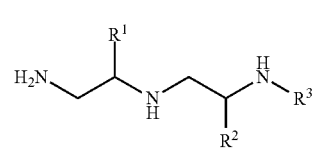

(I)

or a pharmaceutically acceptable salt thereof, wherein
$R^1$ is —$(CH_2)_n$—Y;
Y is NH—X or unsubstituted phenyl;
X is H or methyl;
n is 1, 2, 3, or 4;
$R^2$ is —$(CH_2)_m$—Z;
Z is unsubstituted phenyl or amino;
m is 1, 2, or 3;
$R^3$ is —$(CH_2)_p$-Q;
Q is unsubstituted phenyl; and
p is 1 or 2 and with the proviso that when Y is —NH—X then Z is unsubstituted phenyl, or when Y is unsubstituted phenyl then Z is amino.

2. The compound of claim 1, or a pharmaceutically acceptable salt thereof, wherein Y is —NH—X, and X is methyl.

3. The compound of claim 1, or a pharmaceutically acceptable salt thereof, wherein Y is —NH—X, and X is H.

4. The compound of claim 1, or a pharmaceutically acceptable salt thereof, wherein Y is unsubstituted phenyl.

5. The compound of claim 1, or a pharmaceutically acceptable salt thereof, wherein Z is unsubstituted phenyl.

6. The compound of claim 1, or a pharmaceutically acceptable salt thereof, wherein Z is amino.

7. The compound of claim 1, or a pharmaceutically acceptable salt thereof, wherein the carbon atom to which $R^1$ is attached has (S) configuration.

8. The compound of claim 1, or a pharmaceutically acceptable salt thereof, wherein the carbon atom to which $R^1$ is attached has (R) configuration.

9. The compound of claim 1, or a pharmaceutically acceptable salt thereof, wherein the carbon atom to which $R^2$ is attached has (S) configuration.

10. The compound of claim 1, or a pharmaceutically acceptable salt thereof, wherein the carbon atom to which $R^1$ is attached has (S) configuration, and the carbon atom to which $R^2$ is attached has (S) configuration.

11. The compound of claim 1, or a pharmaceutically acceptable salt thereof, wherein the carbon atom to which $R^1$ is attached has (R) configuration, and the carbon atom to which $R^2$ is attached has (S) configuration.

12. The compound of claim 1, or a pharmaceutically acceptable salt thereof, wherein
$R^1$ is —(CH$_2$)$_n$—Y, Y is —NH—X, X is methyl, n is 4, $R^2$ is —(CH$_2$)$_m$—Z wherein Z is unsubstituted phenyl and m is 1, and $R^3$ is —(CH$_2$)$_p$-Q wherein Q is unsubstituted phenyl and p is 2; or
$R^1$ is —(CH$_2$)$_n$—Y, Y is —NH—X, X is H, n is 2, $R^2$ is —(CH$_2$)$_m$—Z wherein Z is unsubstituted phenyl and m is 1, and $R^3$ is —(CH$_2$)$_p$-Q wherein Q is unsubstituted phenyl and p is 2; or
$R^1$ is —(CH$_2$)$_n$—Y, Y is —NH—X, X is H, n is 3, $R^2$ is —(CH$_2$)$_m$—Z wherein Z is unsubstituted phenyl and m is 1, and $R^3$ is —(CH$_2$)$_p$-Q wherein Q is unsubstituted phenyl and p is 2; or
$R^1$ is —(CH$_2$)$_n$—Y, Y is unsubstituted phenyl, n is 1, $R^2$ is —(CH$_2$)$_m$—Z wherein Z is amino and m is 3, and $R^3$ is —(CH$_2$)$_p$-Q wherein Q is unsubstituted phenyl and p is 2.

13. The compound of claim 1, selected from the group consisting of:

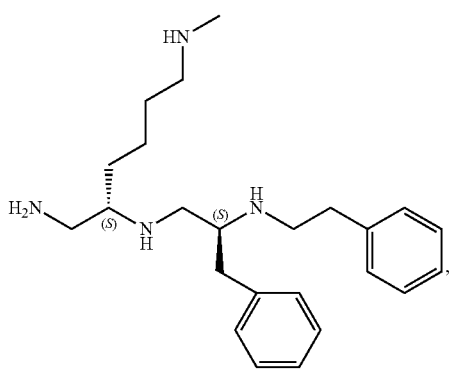

247

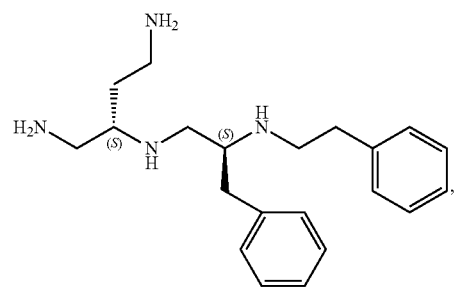

250

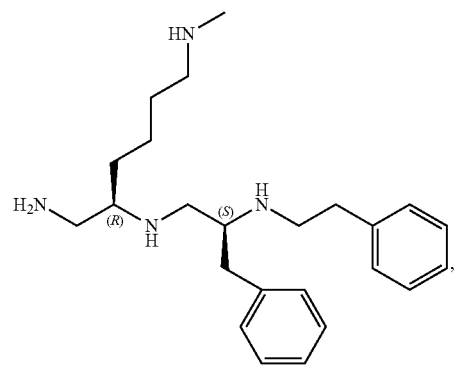

266

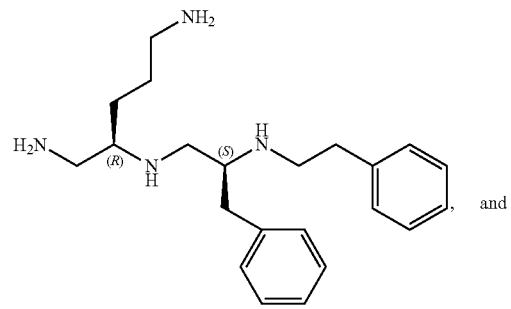

271 and

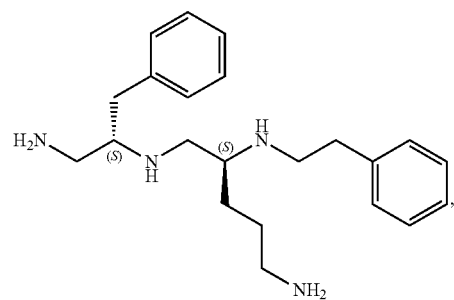

314 or a pharmaceutically acceptable salt thereof.

14. A pharmaceutical composition comprising a therapeutically effective amount of a compound of claim 1, or a pharmaceutically acceptable salt thereof, and a pharmaceutically acceptable carrier.

15. The pharmaceutical composition of claim 14, further comprising an antibiotic.

16. A method of treating antibiotic resistance in a subject, the method comprising administering to the subject a therapeutically effective amount of a compound of claim 1, or a pharmaceutically acceptable salt thereof.

17. A method of treating a bacterial infection in a subject, the method comprising administering to the subject a therapeutically effective amount of a compound of claim 1, or a pharmaceutically acceptable salt thereof.

18. The method of claim 16, wherein the compound or the pharmaceutically acceptable salt thereof is co-administered with at least one antibiotic.

19. The method of claim 17, wherein the compound or the pharmaceutically acceptable salt thereof is co-administered with at least one antibiotic.

\* \* \* \* \*